(12) United States Patent
Tormo i Blasco et al.

(10) Patent No.: US 7,488,732 B2
(45) Date of Patent: Feb. 10, 2009

(54) 2-SUBSTITUTED PYRIMIDINES

(75) Inventors: Jordi Tormo i Blasco, Laudenbach (DE); Carsten Blettner, Hong Kong (CN); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Peter Schäfer, Ottersheim (DE); Frank Schieweck, Heßheim (DE); Anja Schwögler, Mannheim (DE); Oliver Wagner, Neustadt (DE); Maria Scherer, Landau (DE); Siegfried Strathmann, Limburgerhof (DE); Ulrich Schöfl, Brühl (DE); Reinhard Stierl, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 323 days.

(21) Appl. No.: 10/549,936

(22) PCT Filed: Mar. 30, 2004

(86) PCT No.: PCT/EP2004/003335

§ 371 (c)(1),
(2), (4) Date: Sep. 20, 2005

(87) PCT Pub. No.: WO2004/087678

PCT Pub. Date: Oct. 14, 2004

(65) Prior Publication Data

US 2006/0229328 A1    Oct. 12, 2006

(30) Foreign Application Priority Data

Apr. 4, 2003  (DE) .................... 103 15 735

(51) Int. Cl.
C07D 239/28 (2006.01)
C07D 239/34 (2006.01)
C07D 239/42 (2006.01)
C07D 239/46 (2006.01)
A01N 43/54 (2006.01)

(52) U.S. Cl. .................. 514/256; 544/242; 544/334; 544/335

(58) Field of Classification Search ............ 544/242, 544/334, 335; 514/256
See application file for complete search history.

(56) References Cited

U.S. PATENT DOCUMENTS

| 4,876,335 | A | 10/1989 | Yamane et al. |
| 2003/0088096 | A1 | 5/2003 | Pees et al. |
| 2004/0116429 | A1 | 6/2004 | Grote et al. |
| 2004/0147744 | A1 | 7/2004 | Pees et al. |
| 2004/0259887 | A1* | 12/2004 | Dow .................... 514/256 |

FOREIGN PATENT DOCUMENTS

| EP | 0 251 083 A | 1/1988 |
| WO | WO-01/96314 A1 | 12/2001 |
| WO | WO-02/074753 A | 9/2002 |

OTHER PUBLICATIONS

Hodgetts, Kevin J., et al., Bioorganic & Medicinal Chemistry Letters, 13(15), 2497-2500, 2003.

* cited by examiner

Primary Examiner—Deepak Rao
(74) Attorney, Agent, or Firm—Birch, Stewart, Kolasch & Birch, LLP

(57) ABSTRACT

2-Substituted pyrimidines of the formula I

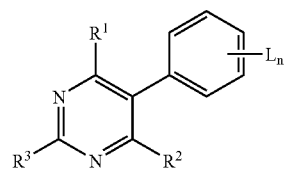

in which the index n and the substituents L, $R^a$, $R^b$, $R^c$, $R^z$, $R^u$, $R^v$, A', A" and A''' are as defined in the description and:

$R^1$ is $C_3$-$C_{10}$-alkyl, $C_3$-$C_{10}$-alkenyl, $C_3$-$C_{10}$-alkynyl, $C_3$-$C_{12}$-cycloalkyl, $C_3$-$C_{10}$-cycloalkenyl or a five- to ten-membered saturated, partially unsaturated or aromatic heterocycle which is attached via carbon and contains one to four heteroatoms from the group consisting of O, N and S, $R^2$ is halogen, cyano, $C_1$-$C_4$-alkyl, $C_2$-$C_4$-alkenyl, $C_2$-$C_4$-alkynyl, $C_1$-$C_4$-alkoxy, $C_3$-$C_4$-alkenyloxy or $C_3$-$C_4$-alkynyloxy, where the alkyl, alkenyl and alkynyl radicals of $R^2$ may be substituted by halogen, cyano, nitro, $C_1$-$C_2$-alkoxy or $C_1$-$C_4$-alkoxycarbonyl, and $R^3$ is cyano, $CO_2R^a$, $C(=O)NR^zR^b$, $C(=O)-N-OR^b$, $C(=S)-NR^aR^b$, $C(=NOR^a)NR^zR^b$, $C(=NR^a)NR^zR^b$, $C(=O)NR^a-NR^zR^b$, $C(=N-NR^zR^c)NR^zR^b$, $C(=O)R^a$, $C(=NOR^b)R^a$, $C(=N-NR^zR^b)R^a$, $CR^aR^b-OR^z$, $CR^aR^b-NR^zR^c$, $ON(=CR^aR^b)$, $O-C(=O)R^a$, $NR^aR^{b'}$, $NR^a(C(=O)R^b)$, $NR^a(C(=O)OR^b)$, $NR^a(C(=O)-NR^zR^b)$, $NR^a(C(=NR^c)R^b)$, $NR^a(N=CR^cR^b)$, $NR^a-NR^zR^b$, $NR^z-OR^a$, $NR^a(C(=NR^c)-NR^zR^b)$, $NR^a(C(=NOR^c)R^b)$, processes for preparing these compounds, compositions comprising these compounds and their pesticidal use are described.

17 Claims, No Drawings

2-SUBSTITUTED PYRIMIDINES

This application is a 371 of PCT/EP04/03335 filed Mar. 30, 2004.

The invention relates to 2-substituted pyrimidines of the formula I

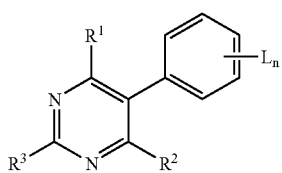

in which the index and the substituents are as defined below:
n is an integer from 1 to 5, where at least one substituent L is located in the ortho-position on the phenyl ring;
L is halogen, cyano, nitro, cyanato (OCN), $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, —C(=S)—N(A')A, —C(=NA')-SA, —C(=O)-A, —C(=O)—O-A, —C(=O)—N(A')A, C(A')(=N—OA), N(A')A, N(A')-C(=O)-A, N(A'')-C(=O)—N(A')A, S(=O)$_m$-A, S(=O)$_m$—O-A or S(=O)$_m$—N(A')A,
m is 0, 1 or 2;
  A, A', A'' independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by cyano or $C_1$-$C_4$-alkoxy; or A and A' together with the atoms to which they are attached are a five- or six-membered saturated, partially unsaturated or aromatic heterocycle which contains one to four heteroatoms from the group consisting of O, N and S;
$R^1$ is $C_3$-$C_{10}$-alkyl, $C_3$-$C_{10}$-alkenyl, $C_3$-$C_{10}$-alkynyl, $C_3$-$C_{12}$-cycloalkyl, $C_3$-$C_{10}$-cycloalkenyl or a five- to ten-membered saturated, partially unsaturated or aromatic heterocycle which is attached via carbon and contains one to four heteroatoms from the group consisting of O, N and S,
$R^2$ is halogen, cyano, $C_1$-$C_4$-alkyl, $C_2$-$C_4$-alkenyl, $C_2$-$C_4$-alkynyl, $C_1$-$C_4$-alkoxy, $C_3$-$C_4$-alkenyloxy or $C_3$-$C_4$-alkynyloxy, where the alkyl, alkenyl and alkynyl radicals of $R^2$ may be substituted by halogen, cyano, nitro, $C_1$-$C_2$-alkoxy or $C_1$-$C_4$-alkoxycarbonyl,
where the aliphatic, alicyclic or aromatic groups of the radical definitions of L, $R^1$ and/or $R^2$ for their part may be partially or fully halogenated or may carry one to four groups $R^u$:
  $R^u$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, —C(=O)-A, —C(=O)—O-A, —C(=O)—N(A')A, C(A')(=N—OA), N(A')A, N(A')-C(=O)-A, N(A'')-C(=O)—N(A')A, S(=O)$_m$-A, S(=O)$_m$—O-A or S(=O)$_m$—N(A')A, where m, A, A', A'' are as defined above and where the aliphatic, alicyclic or aromatic groups for their part may be partially or fully halogenated or may carry one to three groups $R^v$, $R^v$ having the same meaning as $R^u$;

$R^3$ is cyano, $CO_2R^a$, C(=O)$NR^zR^b$, C(=O)—N—$OR^b$, C(=S)—$NR^aR^b$, C(=$NOR^a$)$NR^zR^b$, C(=$NR^a$)$NR^zR^b$, C(=O)$NR^a$—$NR^zR^b$, C(=N—$NR^zR^c$)$NR^aR^b$, C(=O)$R^a$, C(=$NOR^b$)$R^a$, C(=N—$NR^zR^b$)$R^a$, $CR^aR^b$ $OR^z$, $CR^aR^b$—$NR^zR^c$, ON(=$CR^aR^b$), O—C(=O)$R^a$, $NR^aR^{b'}$, $NR^a$(C(=O)$R^b$), $NR^a$(C(=O)$OR^b$), $NR^a$(C(=O)—$NR^zR^b$), $NR^a$(C(=$NR^c$)$R^b$), $NR^a$(N=$CR^cR^b$), $NR^a$—$NR^zR^b$, $NR^z$—$OR^a$, $NR^a$(C(=$NR^c$)—$NR^zR^b$), $NR^a$(C(=$NOR^c$)$R^b$); where
  $R^a$,$R^b$,$R^c$ independently of one another are hydrogen, $C_1$-$C_6$-alkyl, $C_2$-$C_6$-alkenyl, $C_2$-$C_6$-alkynyl, $C_3$-$C_6$-cycloalkyl or $C_4$-$C_6$-cycloalkenyl;
  $R^{b'}$ has the same meanings as $R^b$, except for hydrogen;
  $R^z$ has the same meanings as $R^a$ and may additionally be —CO—$R^a$;
where the aliphatic or alicyclic groups of the radical definitions of $R^a$,$R^b$,$R^c$ or $R^z$ for their part may be partially or fully halogenated or may carry one to four groups $R^w$:
  $R^w$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, and where two of the radicals $R^a$, $R^b$, $R^c$ or $R^z$ together with the atoms to which they are attached may form a five- or six-membered saturated, partially unsaturated or aromatic heterocycle which contains one to four heteroatoms from the group consisting of O, N and S.

Moreover, the invention relates to a process for preparing these compounds, to compositions comprising them and to their use for controlling phytopathogenic harmful fungi.

Fungicidal pyrimidines carrying a cyanamino substituent in the 2-position are known from WO-A 01/96314.

However, in many cases their activity is unsatisfactory. It was an object of the present invention to provide compounds having improved activity.

We have found that this object is achieved by the pyrimidines of the formula I defined at the outset. Moreover, we have found processes for their preparation and compositions comprising them for controlling harmful fungi.

The compounds I can be obtained by different routes.

1) It is possible, for example, to use dichloropyrimidines of the formula V, whose preparation is described in detail in WO-A 02/074753, as starting materials. Generally, initially the substituent $R^1$ is introduced in the 4-position on the pyrimidine ring by coupling with organometallic reagents (see Scheme 1), giving the compounds of the formula VI.

Scheme 1:

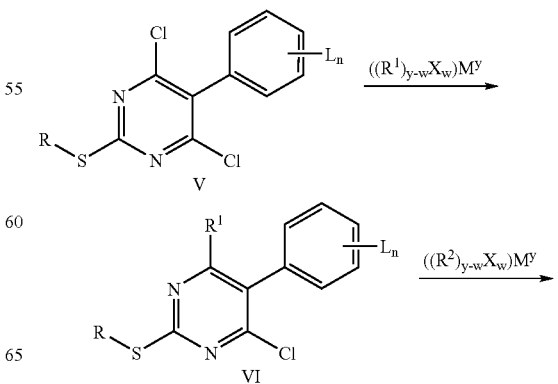

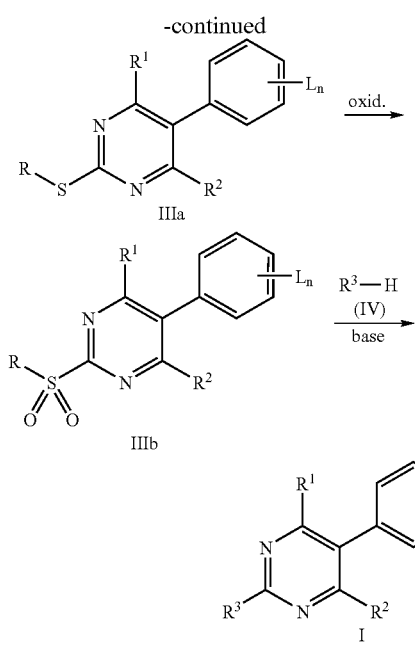

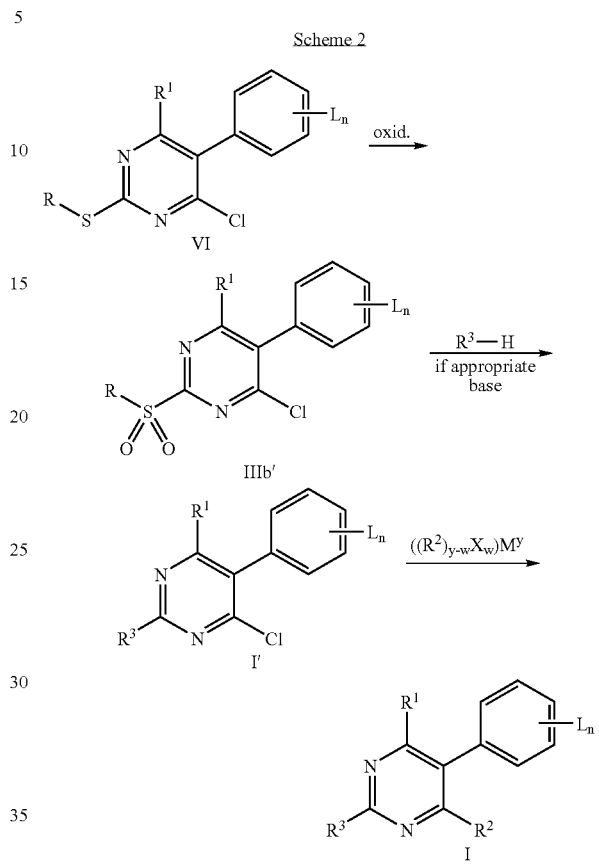

In one embodiment of this process, the reaction is carried out with transition metal catalysis, such as Ni or Pd catalysis. The radical $R^2$ can be introduced analogously into the 6-position on the pyrimidine ring. In some cases it may be advisable to change the order and to introduce the substituent $R^2$ first.

In the formulae $(R^1)_{y-w}X_w\text{-}M^{y'}$ and $(R^2)_{y-w}X_w\text{-}M^{y'}$, M is a metal ion of valency Y, such as, for example, B, Zn, Mg, Cu or Sn, X is chlorine, bromine, iodine or hydroxyl, $R^1$ is preferably $C_3$-$C_8$-alkyl or $C_3$-$C_8$-alkenyl and $R^2$ is in particular $C_1$-$C_4$-alkyl and w is a number from 0 to 3. This reaction can be carried out, for example, analogously to the following methods: J. Chem. Soc. Perkin Trans. 1, 1187 (1994), ibid 1, 2345 (1996); WO-A 99/41255; Aust. J. Chem. 43 (1990), 733; J. Org. Chem. 43 (1978), 358; J. Chem. Soc. Chem. Commun. 866 (1979); Tetrahedron Lett. 34 (1993), 8267; ibid 33 (1992), 413.

What was said above applies in particular to the preparation of compounds in which $R^2$ is an alkyl group. If $R^2$ is a cyano group or an alkoxy substituent, the radical $R^2$ can be introduced by reaction with alkali metal cyanides and alkali metal alkoxides, respectively.

Sulfones of the formula IIIb are obtained by oxidizing the corresponding thio compounds IIIa. They are prepared under the conditions known from WO 02/88127.

Suitable oxidizing agents have been found to be in particular hydrogen peroxide or peracids of organic carboxylic acids. However, the oxidation can also be carried out using, for example, selenium dioxide.

2) Scheme 2 shows a similar synthesis route as Scheme 1 in which only a few synthesis sequences were exchanged. The route shown in Scheme 1 is of interest in particular for preparing the compounds I' in which $R^2$ is chlorine, and for compounds I in which $R^2$ is a cyano or alkoxy group.

The reaction route shown in Scheme 1 allows the introduction of radicals $R^3$ attached via carbon, such as cyano, or radicals attached via nitrogen, such as hydroxylamine, amidine or guanidine, in the 2-position on the pyrimidine ring. Starting from the cyano radical, it is in turn possible to construct other carbon-bound radicals in the 2-position using methods known from the literature: for example the carboxylate radical $CO_2R^a$ by hydrolysis or the acyl radical $C(=O)R^a$ by Grignard reaction.

A further advantageous route for preparing the compounds I is shown in Scheme 3. Here, the substituent $R^{2'}$ is a radical which is attached via carbon, such as alkyl, but not cyano. As already discussed in more detail for the synthesis route shown in Scheme 1, it is possible to synthesize, in the manner mentioned above, various radicals attached via carbon, starting from the cyano radical which is introduced directly.

3) The pyrimidine ring is synthesized using the routes described in WO 97/49697, DD 151404 and JOC 17 (1952), 1320.

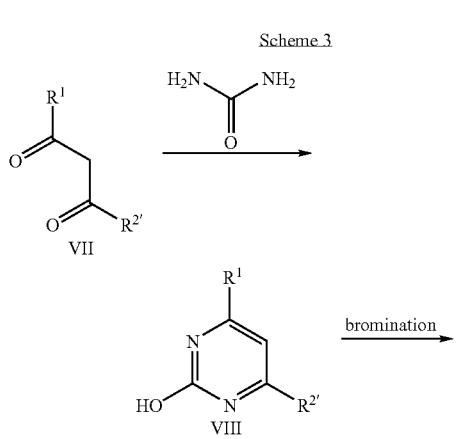

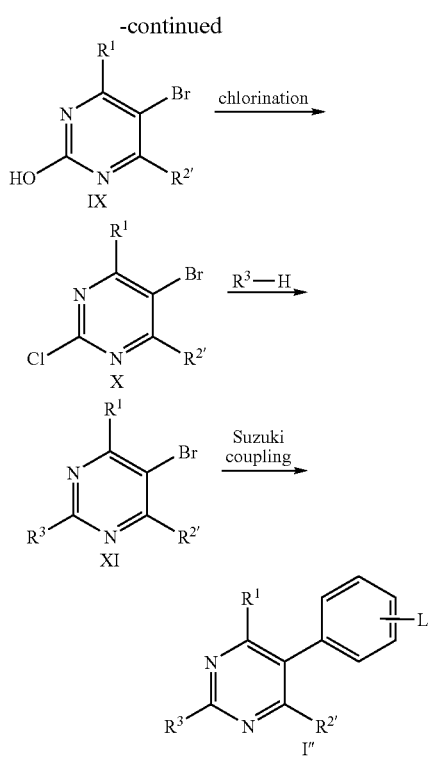

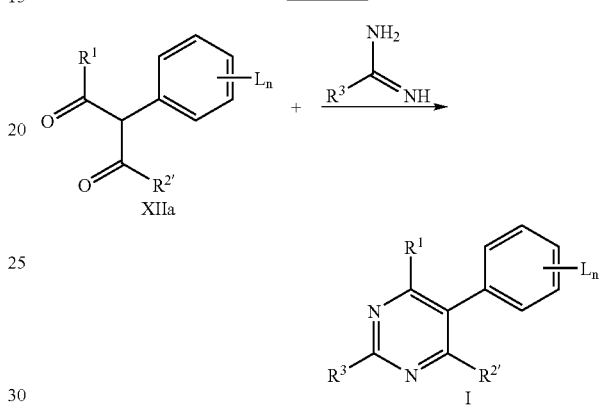

Scheme 4a

The bromination is preferably carried out using elemental bromine or N-bromosuccinimide. This step can advantageously be carried out in an inert solvent, such as chlorobenzene, nitrobenzene, methylene chloride, chloroform, carbon tetrachloride or a carboxylic acid such as acetic acid.

Suitable chlorinating agents [Cl] for converting the hydroxyl compounds IX to the compounds X are, for example, $POCl_3$, $PCl_3/Cl_2$ or $PCl_5$, or mixtures of these reagents. The reaction can be carried out in excess chlorinating agent ($POCl_3$) or in an inert solvent, such as, for example, acetonitrile, toluene, chlorobenzene or 1,2-dichloroethane. Preference is given to carrying out the reaction in $POCl_3$. The chlorinated product can be prepared analogously to the method described in WO 02/74753 on page 4, line 25.

This reaction is usually carried out between 10 and 180° C. For practical reasons, the reaction temperature usually corresponds to the boiling point of the chlorinating agent used ($POCl_3$) or to the boiling point of the solvent. The process is advantageously carried out with addition of N,N-dimethylformamide in catalytic or substoichiometric amounts or of nitrogen bases, such as, for example, N,N-dimethylaniline.

In the case of reagents which are sufficiently nucleophilic, $R^3$ and the pyrimidine ring are attached under the conditions of nucleophilic substitution; usually at from 0 to 200° C., preferably at from 10 to 150° C., in the presence of a dipolar aprotic solvent, such as N,N-dimethylformamide, tetrahydrofuran or acetonitrile [cf. DE-A 39 01 084; Chimia 50 (1996), 525-530; Khim. Geterotsikl. Soedin 12 (1998), 1696-1697].

In general, the components are employed in an approximately stoichiometric ratio. However, it may be advantageous to use an excess of the nucleophile of the formula $R^3$—H.

In general, the reaction is carried out in the presence of a base which can be used in equimolar amounts or else in excess. Suitable bases are alkali metal carbonates and bicarbonates, for example $Na_2CO_3$ and $NaHCO_3$, nitrogen bases, such as triethylamine, tributylamine and pyridine, alkali metal alkoxides, such as sodium methoxide or potassium tert-butoxide, alkali metal amides, such as $NaNH_2$, or else alkali metal hydrides, such as LiH or NaH.

Moreover, the pyridine and the phenyl ring can also be linked under the reaction conditions of the Suzuki coupling (JOC 67 (2002), 3643; Angew. Chem. 114 (2002), 4350, and literature cited therein).

4) When constructing the pyrimidine ring, it may be advantageous to introduce the substituent $R^3$ together with the amidine component, as shown in Scheme 4a. In this, $R^{2'}$ is again a radical attached via carbon, such as alkyl (but not cyano).

If, in the reaction shown in Scheme 4a, the specific amidine component reacted with the 1,3-dicarbonyl compound XIIa is guanidine, 2-aminopyrimidines are obtained. Using alkylating and acylating methods known from the literature, it is thus possible to synthesize in a simple manner pyrimidines according to the invention having a radical attached via nitrogen in the 2-position. In these cases, $R^2$ is preferably a radical attached via carbon (except for cyano). For compounds having this substitution pattern, this is an interesting alternative to methods 1 to 3 mentioned above.

Conversely, pyrimidines I in which $R^2$ is halogen or an alkoxy group can be prepared advantageously using the route shown in Scheme 4b. Using ketoesters XIIb and amidines as starting materials, compounds XIII are obtained which, depending on the nature of the substituent $R^2$, can be converted into the respective target compounds I or I'.

Scheme 4b

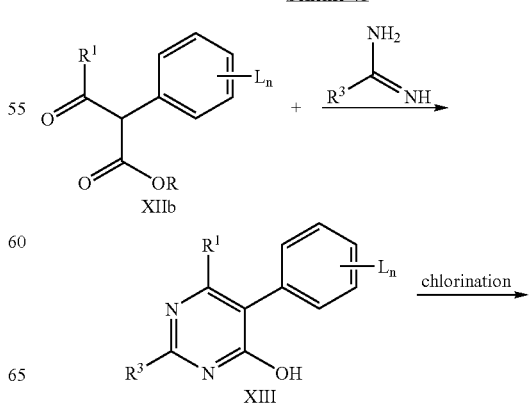

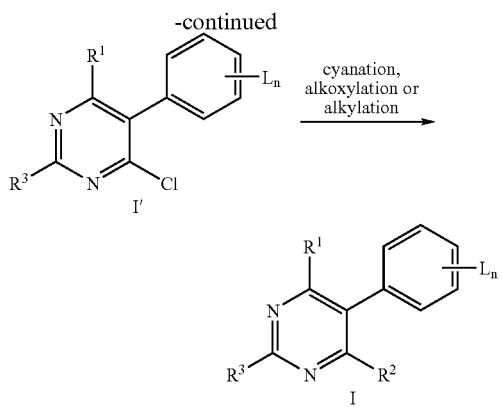

5) As already mentioned repeatedly above, for preparing the pyrimidines I in which $R^3$ is a radical attached via carbon, such as alkyl (but not cyano), it is advantageous to use, as starting materials, 1,3-dicarbonyl compounds (XIIa). Reaction with urea gives—as shown in Scheme 5—the compounds XIV, which can be chlorinated to give XV.

Scheme 5:

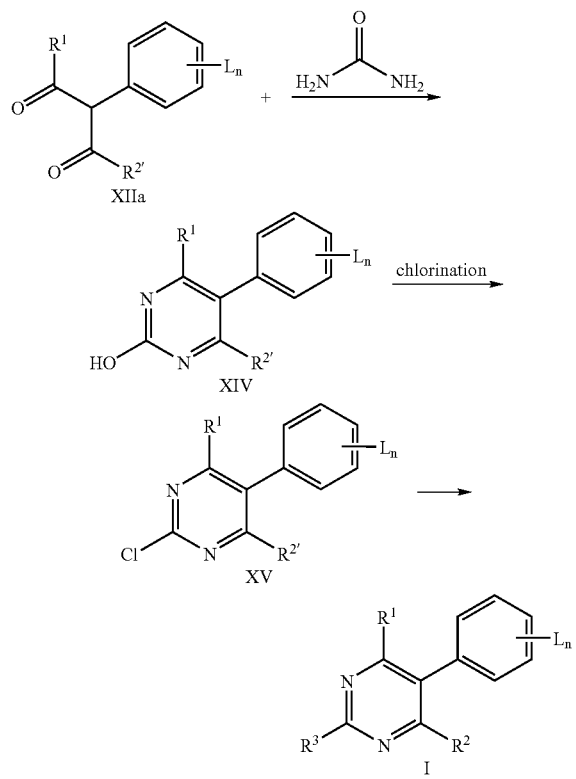

In the case of strong nucleophiles, the substituent $R^3$ (last process step) is introduced under the conditions of nucleophilic substitution.

Moreover, the bond can also be formed with transition metal catalysis, such as, for example, under the reaction conditions of the Suzuki coupling.

6) Scheme 6 additionally shows how the chain of the substituent $R^1$ can be extended.

Scheme 6:

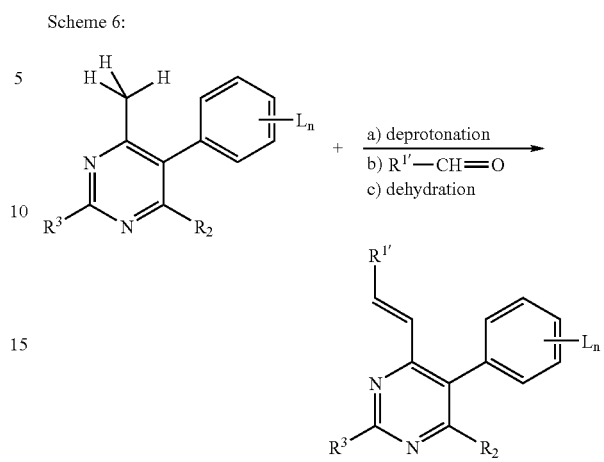

The synthesis route shown in Scheme 7 is similar to those shown in Schemes 2 and 6. Here, initially the chain is extended to construct the lipophilic radical in the 6-position on the pyrimidine ring. The radical $R^3$ is only introduced at the end. This variant is recommended for substituents $R^3$ sensitive to hydrolysis.

Scheme 7

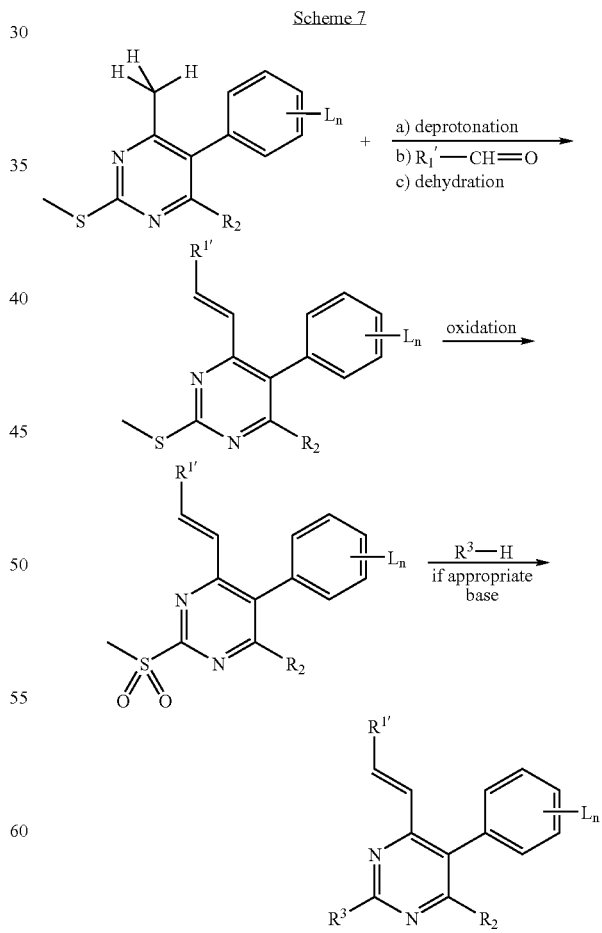

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, purification can also be carried out by recrystallization or digestion.

If individual compounds I cannot be obtained by the routes described above, they can be prepared by derivatization of other compounds I.

If the synthesis yields mixtures of isomers, a separation is generally not necessarily required since in some cases the individual isomers can be converted into one another during work-up for use or during application (for example under the action of light, acids or bases). Such conversions may also take place after use, for example in the treatment of plants in the treated plants or in the harmful fungus to be controlled.

In the definitions of the symbols given in the formulae above, collective terms were used which are generally representative of the following substituents:

halogen: fluorine, chlorine, bromine and iodine;

alkyl: saturated straight-chain or branched hydrocarbon radicals having 1 to 4, 6, 8 or 10 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethyipropyl, 1-ethyl-1-methylpropyl and 1-ethyl-2-methylpropyl;

haloalkyl: straight-chain or branched alkyl groups having 1 to 10 carbon atoms (as mentioned above), where in these groups some or all of the hydrogen atoms may be replaced by halogen atoms as mentioned above, for example $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated straight-chain or branched hydrocarbon radicals having 2 to 4, 6, 8 or 10 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkadienyl: unsaturated straight-chain or branched hydrocarbon radicals having 4, 6, 8 or 10 carbon atoms and two double bonds in any position;

haloalkenyl: unsaturated straight-chain or branched hydrocarbon radicals having 2 to 10 carbon atoms and a double bond in any position (as mentioned above), where in these groups some or all of the hydrogen atoms may be replaced by halogen atoms as mentioned above, in particular by fluorine, chlorine and bromine;

alkynyl: straight-chain or branched hydrocarbon groups having 2 to 4, 6, 8 or 10 carbon atoms and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: mono- or bicyclic saturated hydrocarbon groups having 3 to 6 or 8 carbon ring members, for example $C_3$-$C_8$-cycloalkyl such as cyclopropyl, cyclobutyl, cyclopentyl, cyclohexyl, cycloheptyl and cyclooctyl;

five- or six-membered saturated, partially unsaturated or aromatic heterocycle which contains one to four heteroatoms from the group consisting of O, N and S:

5- or 6-membered heterocyclyl which contains one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol4-yl, 3,4-dihydropyrazol-5-yl, 4,5-dihydropyrazol-1-yl, 4,5-dihydropyrazol-3-yl, 4,5-dihydropyrazol4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol4-yl, 3,4-dihydrooxazol-5-yl, 3,4-dihydrooxazol-2-yl, 3,4-dihydrooxazol-3-yl, 3,4-dihydrooxazol4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl and morpholinyl;

5-membered heteroaryl which contains one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl which contains one to three or one to four nitrogen atoms: 6-membered heteroaryl groups which, in addition to carbon atoms, may contain one to three and one to four nitrogen atoms, respectively, as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The scope of the present invention includes the (R) and (S) isomers and the racemates of compounds of the formula I having chiral centers.

Hereinbelow, the embodiments of the invention are described in more detail.

Pyrimidines I where the index and the substituents are as defined below:

n is an integer from 1 to 5, where at least one substituent L is located in the ortho-position on the phenyl ring L is halogen, cyano, nitro, cyanato (OCN), $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_1$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, —C(=S)—N(A')A, —C(=NA')-SA, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A, m is 0, 1 or 2;

A, A', A" independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by cyano or $C_1$-$C_4$-alkoxy; or A and A' together with the atoms to which they are attached are a five- or six-membered saturated, partially unsaturated or aromatic heterocycle which contains one to four heteroatoms from the group consisting of O, N and S;

$R^1$ is $C_3$-$C_{10}$-alkyl, $C_3$-$C_{10}$-alkenyl, $C_3$-$C_{10}$-alkynyl, $C_3$-$C_{12}$-cycloalkyl, $C_3$-$C_{10}$-cycloalkenyl or a five- to ten-membered saturated, partially unsaturated or aromatic heterocycle which is attached via carbon and contains one to four heteroatoms from the group consisting of O, N and S, $R^2$ is halogen, cyano, $C_1$-$C_4$-alkyl, $C_2$-$C_4$-alkenyl, $C_2$-$C_4$-alkynyl, $C_1$-$C_4$-alkoxy, $C_3$-$C_4$-alkenyloxy or $C_3$-$C_4$-alkynyloxy, where the alkyl, alkenyl and alkynyl radicals of $R^2$ may be substituted by halogen, cyano, nitro, $C_1$-$C_2$-alkoxy or $C_1$-$C_4$-alkoxycarbonyl where the aliphatic, alicyclic or aromatic groups of the radical definitions of L, $R^1$ and/or $R^2$ for their part may be partially or fully halogenated or may carry one to four groups $R^u$:

$R^u$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A') A, where m, A, A', A" are as defined above and where the aliphatic, alicyclic or aromatic groups for their part may be partially or fully halogenated or may carry one to three groups $R^v$, $R^v$ having the same meaning as $R^u$;

$R^3$ is cyano, $CO_2R^a$, C(=O)NR$^z$R$^b$, C(=S)NR$^z$R$^b$, C(=NOR$^a$)NR$^z$R$^b$, C(=NR$^a$)NR$^z$R$^b$, C(=O)NR$^a$—NR$^z$R$^b$, C(=N—NR$^z$R$^c$)NR$^a$R$^b$, C(=O)R$^a$, C(=NOR$^b$)R$^a$, C(=N—NR$^z$R$^b$)R$^a$, CR$^a$R$^b$—OR$^z$, CR$^a$R$^b$—R$^z$R$^c$, ON(=CR$^a$R$^b$), O—C(=O)R$^a$, NR$^a$R$^{b'}$, NR$^a$(C(=O)R$^b$), NR$^a$(C(=O)OR$^b$), NR$^a$(C(=O)—NR$^z$R$^b$), N—R$^a$(C(=NR$^c$)R$^b$), NR$^a$(N=CR$^c$R$^b$), NR$^a$—NR$^z$R$^b$, NR$^a$—OR$^z$, NR$^a$(C(=NR$^c$)—NR$^z$R$^b$), NR$^a$(C(=NOR$^c$)R$^b$); where $R^a$,$R^b$,$R^c$ independently of one another are hydrogen, $C_1$-$C_6$-alkyl, $C_2$-$C_6$-alkenyl, $C_2$-$C_6$-alkynyl, $C_3$-$C_6$-cycloalkyl or $C_4$-$C_6$-cycloalkenyl;

$R^{b'}$ has the same meanings as $R^b$, except for hydrogen;

$R^z$ has the same meanings as $R^a$ and may additionally be —CO—R$^a$;

where the aliphatic or alicyclic groups of the radical definitions of $R^a$,$R^b$,$R^c$ or $R^z$ for their part may be partially or fully halogenated or may carry one to four groups $R^w$:

$R^w$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, and where two of the radicals $R^a$, $R^b$, $R^c$ or $R^z$ together with the atoms to which they are attached may form a five- or six-membered saturated, partially unsaturated or aromatic heterocycle which contains one to four heteroatoms from the group consisting of O, N and S.

With a view to the intended use of the pyrimidines of the formula 1, particular preference is given to the following meanings of the substituents, in each case on their own or in combination:

Preference is given to compounds I in which $R^1$ is $C_3$-$C_8$-alkyl, $C_3$-$C_8$-alkenyl, $C_3$-$C_8$-alkynyl, $C_3$-$C_6$-cycloalkyl or $C_5$-$C_6$-cycloalkenyl.

Particular preference is given to compounds I in which $R^1$ is $C_3$-$C_6$-alkyl or $C_3$-$C_6$-haloalkyl.

In addition, preference is given to compounds I in which $R^1$ is $C_3$-$C_8$-alkenyl or $C_3$-$C_8$-alkynyl.

Moreover, preference is given to compounds I in which $R^1$ is $C_3$-$C_6$-cycloalkyl or $C_5$-$C_6$-cycloalkenyl, which radicals may be substituted by $C_1$-$C_4$-alkyl or halogen.

Particular preference is given to compounds I in which $R^u$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_5$-$C_6$-cycloalkenyl, —C(=O)—O-A, —C(=O)—N(A')A, C(A')(=N—OA), where the aliphatic or alicyclic groups for their part may be partially or fully halogenated or may carry one to three groups $R^v$, $R^v$ having the same meaning as $R^u$.

Particular preference is given to compounds I in which $R^u$ is halogen, cyano, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_3$-$C_6$-cycloalkyl, $C_5$-$C_6$-cycloalkenyl.

Particular preference is also given to compounds I in which $R^2$ is $C_1$-$C_4$-alkyl which may be substituted by halogen.

Moreover, particular preference is given to compounds I in which $R^2$ is halogen, cyano, $C_1$-$C_4$-alkyl or $C_1$-$C_4$-alkoxy.

Especially preferred are compounds I in which $R^2$ is methyl, ethyl, cyano, methoxy or chlorine.

Preference is furthermore given to pyrimidines of the formula I in which $R^3$ is cyano, $CO_2R^a$, $C(=O)NR^zR^b$, $C(=NOR^a)NR^zR^b$, $C(=NR^a)NR^zR^b$, $C(=O)NR^a$—$NR^zR^b$, $C(=N$—$NR^zR^c)NR^aR^b$, $C(=O)R^a$, $C(=NOR^b)R^a$, $C(=O)$—$N(R^a)$—$OR^b$, $C(=S)$—$NR^aR^b$, $C(=N$—$NR^zR^b)R^a$, $CR^aR^b$—$OR^z$ or $CR^aR^b$—$NR^zR^c$.

Particular preference is given to pyrimidines of the formula I in which $R^3$ is cyano, $C(=O)NR^zR^b$, $C(=O)$—$N(R^a)$—$OR^b$, $C(=S)$—$NR^aR^b$, $C(=NOR^a)NR^zR^b$, $C(=NOR^b)R^a$, $C(=N$—$NR^zR^b)R^a$ or $CR^aR^b$—$NR^zR^c$.

Moreover, preference is given to pyrimidines of the formula I in which $R^3$ is ON(=$CR^aR^b$) or O—$C(=O)R^a$.

Furthermore, preference is given to pyrimidines of the formula I in which $R^3$ is $NR^aR^b$, $NR^a(C(=O)R^b)$, $NR^a(C(=O)OR^b)$, $NR^a(C(=O)$—$NR^zR^b)$, $NR^a(C(=NR^a)R^b)$, $NR^a(N=CR^cR^b)$, $NR^a$—$NR^zR^b$, $NR^z$—$OR^a$, $NR^a(C(=NR^c)$—$NR^zR^b)$, $NR^a(C(=NOR^c)R^b)$.

Especially preferred are pyrimidines of the formula I in which $R^3$ is $NR^a(C(=O)R^b)$, $NR^a(C(=O)OR^b)$, $NR^a(N=CR^cR^b)$, $NR^z$—$OR^a$.

$R^a$, $R^b$ and $R^c$ are preferably independently of one another hydrogen, $C_1$-$C_6$-alkyl, $C_2$-$C_6$-alkenyl, $C_2$-$C_6$-alkynyl or $C_3$-$C_6$-cycloalkyl.

$R^z$ preferably has the preferred meanings of $R^a$, $R^b$ and $R^c$ mentioned above. Particular preference is given to the additional meaning —CO—$R^a$.

Moreover, preference is given to pyrimidines I where the phenyl group substituted by $L_n$ is the group B

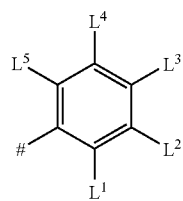

B where # is the point of attachment to the pyrimidine skeleton
$L^1$ is fluorine, chlorine, $CH_3$ or $CF_3$;

$L^2$,$L^4$ independently of one another are hydrogen, $CH_3$ or fluorine;

$L^3$ is hydrogen, fluorine, chlorine, bromine, cyano, nitro, $CH_3$, $SCH_3$, $OCH_3$, $SO_2CH_3$, CO—$NH_2$, CO—$NHCH_3$, CO—$NHC_2H_5$, CO—$N(CH_3)_2$, NH—C(=O)$CH_3$, $N(CH_3)$—C(=O)$CH_3$ or $COOCH_3$ and $L^5$ is hydrogen, fluorine, chlorine or $CH_3$.

Moreover, particular preference is given to pyrimidines I where the index n and the substituents $L^1$ to $L^5$ are as defined below:

n 1 to 3;

L is halogen, cyano, nitro, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, —C(=O)—O-A, —C(=O)—N(A')A, C(A')(=N—OA), N(A')A, N(A')-C(=O)-A or S(=O)$_m$-A;

m is 0, 1 or 2;

A, A', A" independently of one another are hydrogen, $C_1$-$C_6$-alkyl, $C_2$-$C_6$-alkenyl, $C_2$-$C_6$-alkynyl, where the organic radicals may be partially or fully halogenated or may be substituted by cyano or $C_1$-$C_4$-alkoxy, or A and A' together with the atoms to which they are attached are a five- or six-membered saturated heterocycle which contains one to four heteroatoms from the group consisting of O, N and S.

Especially preferred are pyrimidines I where the substituents $L^1$ to $L^5$ are as defined below:

L is halogen, cyano, $C_1$-$C_8$-alkyl, $C_1$-$C_6$-alkoxy, —C(=O)—O-A, —C(=O)—N(A')A, A, A', A" independently of one another are hydrogen, $C_1$-$C_6$-alkyl, $C_2$-$C_6$-alkenyl, $C_2$-$C_6$-alkynyl.

In particular with a view to their use, preference is given to the compounds I compiled in the tables below. Moreover, the groups mentioned for a substituent in the tables are per se, independently of the combination in which they are mentioned, a particularly preferred embodiment of the substituent in question.

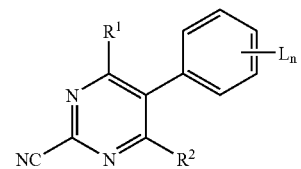

IA

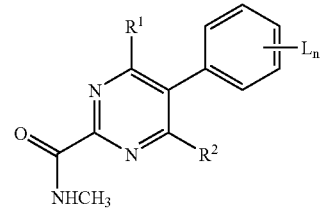

IB

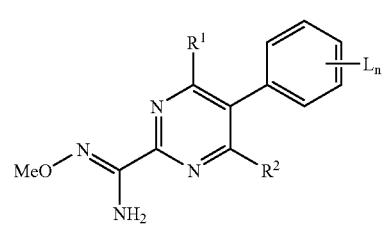

IC

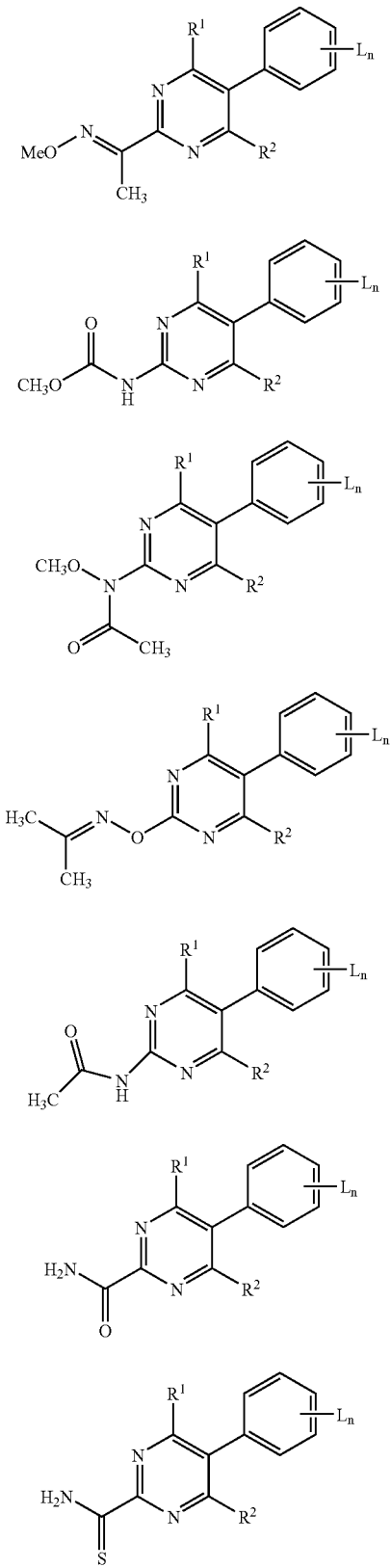

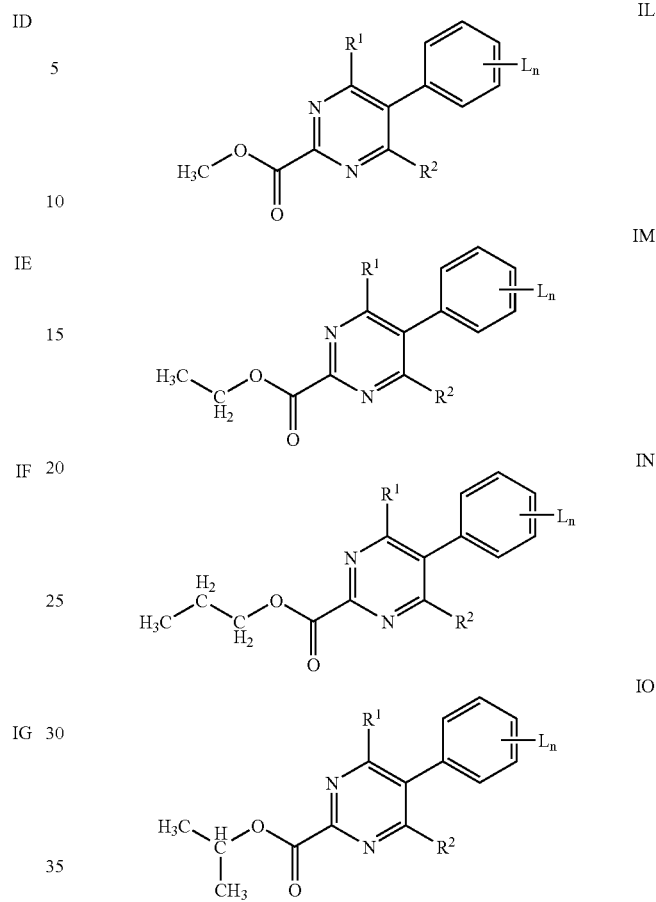

Table 1
Compounds of the formula IA, IB, IC, ID, IE, IF, IG, IH, II, IK, IL, IM, IN and IO in which $L_n$ is 2-fluoro,6-chloro, $R^2$ is methyl and $R^1$ corresponds for each compound to one row of Table A Table 2
Compounds of the formula IA, IB, IC, ID, IE, IF, IG, IH, II, IK, IL, IM, IN and IO in which $L_n$ is 2,6-difluoro, $R^2$ is methyl and $R^1$ corresponds for each compound to one row of Table A Table 3
Compounds of the formula IA, IB, IC, ID, IE, IF, IG, IH, II, IK, IL, IM, IN and IO in which $L_n$ is 2,6-dichloro, $R^2$ is methyl and $R^1$ corresponds for each compound to one row of Table A Table 4
Compounds of the formula IA, IB, IC, ID, IE, IF, IG, IH, II, IK, IL, IM, IN and IO in which $L_n$ is 2-fluoro,6-methyl, $R^2$ is methyl and $R^1$ corresponds for each compound to one row of Table A Table 5
Compounds of the formula IA, IB, IC, ID, IE, IF, IG, IH, II, IK, IL, IM, IN and IO in which $L_n$ is 2,4,6-trifluoro, $R^2$ is methyl and $R^1$ corresponds for each compound to one row of Table A Table 6
Compounds of the formula IA, IB, IC, ID, IE, IF, IG, IH, II, IK, IL, IM, IN and IO in which $L_n$ is 2-methyl,4-fluoro, $R^2$ is methyl and $R^1$ corresponds for each compound to one row of Table A Table 7
Compounds of the formula IA, IB, IC, ID, IE, IF, IG, IH, II, IK, IL, IM, IN and IO in which $L_n$ is 2-fluoro,4-methoxycarbonyl, $R^2$ is methyl and $R^1$ corresponds for each compound to one row of Table A Table 8
Compounds of the formula IA, IB, IC, ID, IE, IF, IG, IH, II, IK, IL, IM, IN and IO in which $L_n$ is 2-fluoro,4-CN, $R^2$ is methyl and $R^1$ corresponds for each compound to one row of Table A Table 9
Compounds of the formula IA, IB, IC, ID, IE, IF, IG, IH, II, IK, IL, IM, IN and IO in which $L_n$ is 2,4,5-trifluoro, $R^2$ is methyl and $R^1$ corresponds for each compound to one row of Table A Table 10
Compounds of the formula IA, IB, IC, ID, IE, IF, IG, IH, II, IK, IL, IM, IN and IO in which $L_n$ is 2,4-dichloro, $R^2$ is methyl and $R^1$ corresponds for each compound to one row of Table A Table 11
Compounds of the formula IA, IB, IC, ID, IE, IF, IG, IH, II, IK, IL, IM, IN and IO in which $L_n$ is 2-chloro, $R^2$ is methyl and $R^1$ corresponds for each compound to one row of Table A Table 12
Compounds of the formula IA, IB, IC, ID, IE, IF, IG, IH, II, IK, IL, IM, IN and IO in which $L_n$ is 2-fluoro, $R^2$ is methyl and $R^1$ corresponds for each compound to one row of Table A Table 13
Compounds of the formula IA, IB, IC, ID, IE, IF, IG, IH, II, IK, IL, IM, IN and IO in which $L_n$ is 2,4-difluoro, $R^2$ is methyl and $R^1$ corresponds for each compound to one row of Table A Table 14
Compounds of the formula IA, IB, IC, ID, IE, IF, IG, IH, II, IK, IL, IM, IN and IO in which $L_n$ is 2-fluoro,4-chloro, $R^2$ is methyl and $R^1$ corresponds for each compound to one row of Table A Table 15
Compounds of the formula IA, IB, IC, ID, IE, IF, IG, IH, II, IK, IL, IM, IN and IO in which $L_n$ is 2-chloro,4-fluoro, $R^2$ is methyl and $R^1$ corresponds for each compound to one row of Table A Table 16
Compounds of the formula IA, IB, IC, ID, IE, IF, IG, IH, II, IK, IL, IM, IN and IO in which $L_n$ is 2,3-difluoro, $R^2$ is methyl and $R^1$ corresponds for each compound to one row of Table A Table 17
Compounds of the formula IA, IB, IC, ID, IE, IF, IG, IH, II, IK, IL, IM, IN and IO in which $L_n$ is 2,5-difluoro, $R^2$ is methyl and $R^1$ corresponds for each compound to one row of Table A Table 18
Compounds of the formula IA, IB, IC, ID, IE, IF, IG, IH, II, IK, IL, IM, IN and IO in which $L_n$ is 2,3,4-trifluoro, $R^2$ is methyl and $R^1$ corresponds for each compound to one row of Table A Table 19
Compounds of the formula IA, IB, IC, ID, IE, IF, IG, IH, II, IK, IL, IM, IN and IO in which $L_n$ is 2-methyl, $R^2$ is methyl and $R^1$ corresponds for each compound to one row of Table A Table 20
Compounds of the formula IA, IB, IC, ID, IE, IF, IG, IH, II, IK, IL, IM, IN and IO in which $L_n$ is 2,4-dimethyl, $R^2$ is methyl and $R^1$ corresponds for each compound to one row of Table A Table 21
Compounds of the formula IA, IB, IC, ID, IE, IF, IG, IH, II, IK, IL, IM, IN and IO in which $L_n$ is 2-methyl,4-chloro, $R^2$ is methyl and $R^1$ corresponds for each compound to one row of Table A Table 22
Compounds of the formula IA, IB, IC, ID, IE, IF, IG, IH, II, IK, IL, IM, IN and IO in which $L_n$ is 2-fluoro,4-methyl, $R^2$ is methyl and $R^1$ corresponds for each compound to one row of Table A Table 23
Compounds of the formula IA, IB, IC, ID, IE, IF, IG, IH, II, IK, IL, IM, IN and IO in which $L_n$ is 2,6-dimethyl, $R^2$ is methyl and $R^1$ corresponds for each compound to one row of Table A Table 24
Compounds of the formula IA, IB, IC, ID, IE, IF, IG, IH, II, IK, IL, IM, IN and IO in which $L_n$ is 2,4,6-trimethyl, $R^2$ is methyl and $R^1$ corresponds for each compound to one row of Table A Table 25
Compounds of the formula IA, IB, IC, ID, IE, IF, IG, IH, II, IK, IL, IM, IN and IO in which $L_n$ is 2,6-difluoro,4-cyano, $R^2$ is methyl and $R^1$ corresponds for each compound to one row of Table A Table 26
Compounds of the formula IA, IB, IC, ID, IE, IF, IG, IH, II, IK, IL, IM, IN and IO in which $L_n$ is 2,6-difluoro,4-methyl, $R^2$ is methyl and $R^1$ corresponds for each compound to one row of Table A Table 27
Compounds of the formula IA, IB, IC, ID, IE, IF, IG, IH, II, IK, IL, IM, IN and IO in which $L_n$ is 2,6-difluoro,4-methoxycarbonyl, $R^2$ is methyl and $R^1$ corresponds for each compound to one row of Table A Table 28
Compounds of the formula IA, IB, IC, ID, IE, IF, IG, IH, II, IK, IL, IM, IN and IO in which $L_n$ is 2-chloro,4-methoxy, $R^2$ is methyl and $R^1$ corresponds for each compound to one row of Table A Table 29
Compounds of the formula IA, IB, IC, ID, IE, IF, IG, IH, II, IK, IL, IM, IN and IO in which $L_n$ is 2-chloro,4-methyl, $R^2$ is methyl and $R^1$ corresponds for each compound to one row of Table A Table 30
Compounds of the formula IA, IB, IC, ID, IE, IF, IG, IH, II, IK, IL, IM, IN and IO in which $L_n$ is 2-chloro,4-methoxycarbonyl, $R^2$ is methyl and $R^1$ corresponds for each compound to one row of Table A Table 31
Compounds of the formula IA, IB, IC, ID, IE, IF, IG, IH, II, IK, IL, IM, IN and IO in which $L_n$ is 2-chloro,4-bromo, $R^2$ is methyl and $R^1$ corresponds for each compound to one row of Table A Table 32
Compounds of the formula IA, IB, IC, ID, IE, IF, IG, IH, II, IK, IL, IM, IN and IO in which $L_n$ is 2-chloro,4-cyano, $R^2$ is methyl and $R^1$ corresponds for each compound to one row of Table A Table 33
Compounds of the formula IA, IB, IC, ID, IE, IF, IG, IH, II, IK, IL, IM, IN and IO in which $L_n$ is 2,6-difluoro,4-methoxy, $R^2$ is methyl and $R^1$ corresponds for each compound to one row of Table A Table 34
Compounds of the formula IA, IB, IC, ID, IE, IF, IG, IH, II, IK, IL, IM, IN and IO in which $L_n$ is 2-fluoro,3-methyl, $R^2$ is methyl and $R^1$ corresponds for each compound to one row of Table A Table 35
Compounds of the formula IA, IB, IC, ID, IE, IF, IG, IH, II, IK, IL, IM, IN and IO in which $L_n$ is 2,5-dimethyl, $R^2$ is methyl and $R^1$ corresponds for each compound to one row of Table A Table 36
Compounds of the formula IA, IB, IC, ID, IE, IF, IG, IH, II, IK, IL, IM, IN and IO in which $L_n$ is 2-methyl,4-cyano, $R^2$ is methyl and $R^1$ corresponds for each compound to one row of Table A Table 37
Compounds of the formula IA, IB, IC, ID, IE, IF, IG, IH, II, IK, IL, IM, IN and IO in which $L_n$ is 2-methyl,4-bromo, $R^2$ is methyl and $R^1$ corresponds for each compound to one row of Table A Table 38
Compounds of the formula IA, IB, IC, ID, IE, IF, IG, IH, II, IK, IL, IM, IN and IO in which $L_n$ is 2-methyl,5-fluoro, $R^2$ is methyl and $R^1$ corresponds for each compound to one row of Table A Table 39
Compounds of the formula IA, IB, IC, ID, IE, IF, IG, IH, II, IK, IL, IM, IN and IO in which $L_n$ is 2-methyl,4-methoxy, $R^2$ is methyl and $R^1$ corresponds for each compound to one row of Table A Table 40
Compounds of the formula IA, IB, IC, ID, IE, IF, IG, IH, II, IK, IL, IM, IN and IO in which $L_n$ is 2-methyl,4-methoxycarbonyl, $R^2$ is methyl and $R^1$ corresponds for each compound to one row of Table A Table 41
Compounds of the formula IA, IB, IC, ID, IE, IF, IG, IH, II, IK, IL, IM, IN and IO in which $L_n$ is 2,5-dimethyl,4-brom, $R^2$ is methyl and $R^1$ corresponds for each compound to one row of Table A Table 42
Compounds of the formula IA, IB, IC, ID, IE, IF, IG, IH, II, IK, IL, IM, IN and IO in which $L_n$ is 2-fluoro,4-bromo, $R^2$ is methyl and $R^1$ corresponds for each compound to one row of Table A Table 43
Compounds of the formula IA, IB, IC, ID, IE, IF, IG, IH, II, IK, IL, IM, IN and IO in which $L_n$ is 2-fluoro,4-methoxy, $R^2$ is methyl and $R^1$ corresponds for each compound to one row of Table A Table 44
Compounds of the formula IA, IB, IC, ID, IE, IF, IG, IH, II, IK, IL, IM, IN and IO in which $L_n$ is 2-fluoro,5-methyl, $R^2$ is methyl and $R^1$ corresponds for each compound to one row of Table A Table 45
Compounds of the formula IA, IB, IC, ID, IE, IF, IG, IH, II, IK, IL, IM, IN and IO in which $L_n$ is pentafluoro, $R^2$ is methyl and $R^1$ corresponds for each compound to one row of Table A Table 46
Compounds of the formula IA, IB, IC, ID, IE, IF, IG, IH, II, IK, IL, IM, IN and IO in which $L_n$ is 2-fluoro,6-chloro, $R^2$ is chloro and $R^1$ corresponds for each compound to one row of Table A Table 47
Compounds of the formula IA, IB, IC, ID, IE, IF, IG, IH, II, IK, IL, IM, IN and IO in which $L_n$ is 2,6-difluoro, $R^2$ is chloro and $R^1$ corresponds for each compound to one row of Table A Table 48
Compounds of the formula IA, IB, IC, ID, IE, IF, IG, IH, II, IK, IL, IM, IN and IO in which $L_n$ is 2,6-dichloro, $R^2$ is chloro and $R^1$ corresponds for each compound to one row of Table A Table 49
Compounds of the formula IA, IB, IC, ID, IE, IF, IG, IH, II, IK, IL, IM, IN and IO in which $L_n$ is 2-fluoro,6-methyl, $R^2$ is chloro and $R^1$ corresponds for each compound to one row of Table A Table 50
Compounds of the formula IA, IB, IC, ID, IE, IF, IG, IH, II, IK, IL, IM, IN and IO in which $L_n$ is 2,4,6-trifluoro, $R^2$ is chloro and $R^1$ corresponds for each compound to one row of Table A Table 51
Compounds of the formula IA, IB, IC, ID, IE, IF, IG, IH, II, IK, IL, IM, IN and IO in which $L_n$ is 2-methyl,4-fluoro, $R^2$ is chloro and $R^1$ corresponds for each compound to one row of Table A Table 52
Compounds of the formula IA, IB, IC, ID, IE, IF, IG, IH, II, IK, IL, IM, IN and IO in which $L_n$ is 2-fluoro,4-methoxycarbonyl, $R^2$ is chloro and $R^1$ corresponds for each compound to one row of Table A Table 53
Compounds of the formula IA, IB, IC, ID, IE, IF, IG, IH, II, IK, IL, IM, IN and IO in which $L_n$ is 2-fluoro,4-CN, $R^2$ is chloro and $R^1$ corresponds for each compound to one row of Table A Table 54
Compounds of the formula IA, IB, IC, ID, IE, IF, IG, IH, II, IK, IL, IM, IN and IO in which $L_n$ is 2,4,5-trifluoro, $R^2$ is chloro and $R^1$ corresponds for each compound to one row of Table A Table 55
Compounds of the formula IA, IB, IC, ID, IE, IF, IG, IH, II, IK, IL, IM, IN and IO in which $L_n$ is 2,4-dichloro, $R^2$ is chloro and $R^1$ corresponds for each compound to one row of Table A Table 56
Compounds of the formula IA, IB, IC, ID, IE, IF, IG, IH, II, IK, IL, IM, IN and IO in which $L_n$ is 2-chloro, $R^2$ is chloro and $R^1$ corresponds for each compound to one row of Table A Table 57
Compounds of the formula IA, IB, IC, ID, IE, IF, IG, IH, II, IK, IL, IM, IN and IO in which $L_n$ is 2-fluoro, $R^2$ is chloro and $R^1$ corresponds for each compound to one row of Table A Table 58
Compounds of the formula IA, IB, IC, ID, IE, IF, IG, IH, II, IK, IL, IM, IN and IO in which $L_n$ is 2,4-difluoro, $R^2$ is chloro and $R^1$ corresponds for each compound to one row of Table A Table 59
Compounds of the formula IA, IB, IC, ID, IE, IF, IG, IH, II, IK, IL, IM, IN and IO in which $L_n$ is 2-fluoro,4-chloro, $R^2$ is chloro and $R^1$ corresponds for each compound to one row of Table A Table 60
Compounds of the formula IA, IB, IC, ID, IE, IF, IG, IH, II, IK, IL, IM, IN and IO in which $L_n$ is 2-chloro,4-fluoro, $R^2$ is chloro and $R^1$ corresponds for each compound to one row of Table A Table 61
Compounds of the formula IA, IB, IC, ID, IE, IF, IG, IH, II, IK, IL, IM, IN and IO in which $L_n$ is 2,3-difluoro, $R^2$ is chloro and $R^1$ corresponds for each compound to one row of Table A Table 62
Compounds of the formula IA, IB, IC, ID, IE, IF, IG, IH, II, IK, IL, IM, IN and IO in which $L_n$ is 2,5-difluoro, $R^2$ is chloro and $R^1$ corresponds for each compound to one row of Table A Table 63
Compounds of the formula IA, IB, IC, ID, IE, IF, IG, IH, II, IK, IL, IM, IN and IO in which $L_n$ is 2,3,4-trifluoro, $R^2$ is chloro and $R^1$ corresponds for each compound to one row of Table A Table 64
Compounds of the formula IA, IB, IC, ID, IE, IF, IG, IH, II, IK, IL, IM, IN and IO in which $L_n$ is 2-methyl, $R^2$ is chloro and $R^1$ corresponds for each compound to one row of Table A Table 65
Compounds of the formula IA, IB, IC, ID, IE, IF, IG, IH, II, IK, IL, IM, IN and IO in which $L_n$ is 2,4-dimethyl, $R^2$ is chloro and $R^1$ corresponds for each compound to one row of Table A Table 66
Compounds of the formula IA, IB, IC, ID, IE, IF, IG, IH, II, IK, IL, IM, IN and IO in which $L_n$ is 2-methyl,4-chloro, $R^2$ is chloro and $R^1$ corresponds for each compound to one row of Table A Table 67
Compounds of the formula IA, IB, IC, ID, IE, IF, IG, IH, II, IK, IL, IM, IN and IO in which $L_n$ is 2-fluoro,4-methyl, $R^2$ is chloro and $R^1$ corresponds for each compound to one row of Table A Table 68
Compounds of the formula IA, IB, IC, ID, IE, IF, IG, IH, II, IK, IL, IM, IN and IO in which $L_n$ is 2,6-dimethyl, R2 is chloro and $R^1$ corresponds for each compound to one row of Table A Table 69
Compounds of the formula IA, IB, IC, ID, IE, IF, IG, IH, II, IK, IL, IM, IN and IO in which $L_n$ is 2,4,6-trimethyl, $R^2$ is chloro and $R^1$ corresponds for each compound to one row of Table A Table 70
Compounds of the formula IA, IB, IC, ID, IE, IF, IG, IH, II, IK, IL, IM, IN and IO in which $L_n$ is 2,6-difluoro,4-cyano, $R^2$ is chloro and $R^1$ corresponds for each compound to one row of Table A Table 71
Compounds of the formula IA, IB, IC, ID, IE, IF, IG, IH, II, IK, IL, IM, IN and IO in which $L_n$ is 2,6-difluoro,4-methyl, $R^2$ is chloro and $R^1$ corresponds for each compound to one row of Table A Table 72
Compounds of the formula IA, IB, IC, ID, IE, IF, IG, IH, II, IK, IL, IM, IN and IO in which $L_n$ is 2,6-difluoro,4-methoxycarbonyl, $R^2$ is chloro and $R^1$ corresponds for each compound to one row of Table A Table 73
Compounds of the formula IA, IB, IC, ID, IE, IF, IG, IH, II, IK, IL, IM, IN and IO in which $L_n$ is 2-chloro,4-methoxy, $R^2$ is chloro and $R^1$ corresponds for each compound to one row of Table A Table 74
Compounds of the formula IA, IB, IC, ID, IE, IF, IG, IH, II, IK, IL, IM, IN and IO in which $L_n$ is 2-chloro,4-methyl, $R^2$ is chloro and $R^1$ corresponds for each compound to one row of Table A Table 75
Compounds of the formula IA, IB, IC, ID, IE, IF, IG, IH, II, IK, IL, IM, IN and IO in which $L_n$ is 2-chloro,4-methoxycarbonyl, $R^2$ is chloro and $R^1$ corresponds for each compound to one row of Table A Table 76
Compounds of the formula IA, IB, IC, ID, IE, IF, IG, IH, II, IK, IL, IM, IN and IO in which $L_n$ is 2-chloro,4-bromo, $R^2$ is chloro and $R^1$ corresponds for each compound to one row of Table A Table 77
Compounds of the formula IA, IB, IC, ID, IE, IF, IG, IH, II, IK, IL, IM, IN and IO in which $L_n$ is 2-chloro,4-cyano, $R^2$ is chloro and $R^1$ corresponds for each compound to one row of Table A Table 78
Compounds of the formula IA, IB, IC, ID, IE, IF, IG, IH, II, IK, IL, IM, IN and IO in which $L_n$ is 2,6-difluoro,4-methoxy, $R^2$ is chloro and $R^1$ corresponds for each compound to one row of Table A Table 79
Compounds of the formula IA, IB, IC, ID, IE, IF, IG, IH, II, IK, IL, IM, IN and IO in which $L_n$ is 2-fluoro,3-methyl, $R^2$ is chloro and $R^1$ corresponds for each compound to one row of Table A Table 80
Compounds of the formula IA, IB, IC, ID, IE, IF, IG, IH, II, IK, IL, IM, IN and IO in which $L_n$ is 2,5-dimethyl, $R^2$ is chloro and $R^1$ corresponds for each compound to one row of Table A Table 81
Compounds of the formula IA, IB, IC, ID, IE, IF, IG, IH, II, IK, IL, IM, IN and IO in which $L_n$ is 2-methyl,4-cyano, $R^2$ is chloro and $R^1$ corresponds for each compound to one row of Table A Table 82
Compounds of the formula IA, IB, IC, ID, IE, IF, IG, IH, II, IK, IL, IM, IN and IO in which $L_n$ is 2-methyl,4-bromo, $R^2$ is chloro and $R^1$ corresponds for each compound to one row of Table A Table 83
Compounds of the formula IA, IB, IC, ID, IE, IF, IG, IH, II, IK, IL, IM, IN and IO in which $L_n$ is 2-methyl,5-fluoro, $R^2$ is chloro and $R^1$ corresponds for each compound to one row of Table A Table 84
Compounds of the formula IA, IB, IC, ID, IE, IF, IG, IH, II, IK, IL, IM, IN and IO in which $L_n$ is 2-methyl,4-methoxy, $R^2$ is chloro and $R^1$ corresponds for each compound to one row of Table A Table 85
Compounds of the formula IA, IB, IC, ID, IE, IF, IG, IH, II, IK, IL, IM, IN and IO in which $L_n$ is 2-methyl,4-methoxycarbonyl, $R^2$ is chloro and $R^1$ corresponds for each compound to one row of Table A Table 86
Compounds of the formula IA, IB, IC, ID, IE, IF, IG, IH, II, IK, IL, IM, IN and IO in which $L_n$ is 2,5-dimethyl,4-bromo, $R^2$ is chloro and $R^1$ corresponds for each compound to one row of Table A Table 87
Compounds of the formula IA, IB, IC, ID, IE, IF, IG, IH, II, IK, IL, IM, IN and IO in which $L_n$ is 2-fluoro,4-bromo, $R^2$ is chloro and $R^1$ corresponds for each compound to one row of Table A Table 88
Compounds of the formula IA, IB, IC, ID, IE, IF, IG, IH, II, IK, IL, IM, IN and IO in which $L_n$ is 2-fluoro,4-methoxy, $R^2$ is chloro and $R^1$ corresponds for each compound to one row of Table A Table 89
Compounds of the formula IA, IB, IC, ID, IE, IF, IG, IH, II, IK, IL, IM, IN and IO in which $L_n$ is 2-fluoro,5-methyl, $R^2$ is chloro and $R^1$ corresponds for each compound to one row of Table A Table 90
Compounds of the formula IA, IB, IC, ID, IE, IF, IG, IH, II, IK, IL, IM, IN and IO in which $L_n$ is pentafluoro, $R^2$ is chloro and $R^1$ corresponds for each compound to one row of Table A Table 91
Compounds of the formula IA, IB, IC, ID, IE, IF, IG, IH, II, IK, IL, IM, IN and IO in which $L_n$ is 2-fluoro,6-chloro, $R^2$ is methoxy and $R^1$ corresponds for each compound to one row of Table A Table 92
Compounds of the formula IA, IB, IC, ID, IE, IF, IG, IH, II, IK, IL, IM, IN and IO in which $L_n$ is 2,6-difluoro, $R^2$ is methoxy and $R^1$ corresponds for each compound to one row of Table A Table 93
Compounds of the formula IA, IB, IC, ID, IE, IF, IG, IH, II, IK, IL, IM, IN and IO in which $L_n$ is 2,6-dichloro, $R^2$ is methoxy and $R^1$ corresponds for each compound to one row of Table A Table 94
Compounds of the formula IA, IB, IC, ID, IE, IF, IG, IH, II, IK, IL, IM, IN and IO in which $L_n$ is 2-fluoro,6-methyl, $R^2$ is methoxy and $R^1$ corresponds for each compound to one row of Table A Table 95
Compounds of the formula IA, IB, IC, ID, IE, IF, IG, IH, II, IK, IL, IM, IN and IO in which $L_n$ is 2,4,6-trifluoro, $R^2$ is methoxy and $R^1$ corresponds for each compound to one row of Table A Table 96
Compounds of the formula IA, IB, IC, ID, IE, IF, IG, IH, II, IK, IL, IM, IN and IO in which $L_n$ is 2-methyl,4-fluoro, $R^2$ is methoxy and $R^1$ corresponds for each compound to one row of Table A Table 97
Compounds of the formula IA, IB, IC, ID, IE, IF, IG, IH, II, IK, IL, IM, IN and IO in which $L_n$ is 2-fluoro,4-methoxycarbonyl, $R^2$ is methoxy and $R^1$ corresponds for each compound to one row of Table A Table 98
Compounds of the formula IA, IB, IC, ID, IE, IF, IG, IH, II, IK, IL, IM, IN and IO in which $L_n$ is 2-fluoro,4-CN, $R^2$ is methoxy and $R^1$ corresponds for each compound to one row of Table A Table 99
Compounds of the formula IA, IB, IC, ID, IE, IF, IG, IH, II, IK, IL, IM, IN and IO in which $L_n$ is 2,4,5-trifluoro, $R^2$ is methoxy and $R^1$ corresponds for each compound to one row of Table A Table 100
Compounds of the formula IA, IB, IC, ID, IE, IF, IG, IH, II, IK, IL, IM, IN and IO in which $L_n$ is 2,4-dichloro, $R^2$ is methoxy and $R^1$ corresponds for each compound to one row of Table A Table 101
Compounds of the formula IA, IB, IC, ID, IE, IF, IG, IH, II, IK, IL, IM, IN and IO in which $L_n$ is 2-chloro, $R^2$ is methoxy and $R^1$ corresponds for each compound to one row of Table A Table 102
Compounds of the formula IA, IB, IC, ID, IE, IF, IG, IH, II, IK, IL, IM, IN and IO in which $L_n$ is 2-fluoro, $R^2$ is methoxy and $R^1$ corresponds for each compound to one row of Table A Table 103
Compounds of the formula IA, IB, IC, ID, IE, IF, IG, IH, II, IK, IL, IM, IN and IO in which $L_n$ is 2,4-difluoro, $R^2$ is methoxy and $R^1$ corresponds for each compound to one row of Table A Table 104
Compounds of the formula IA, IB, IC, ID, IE, IF, IG, IH, II, IK, IL, IM, IN and IO in which $L_n$ is 2-fluoro,4-chloro, $R^2$ is methoxy and $R^1$ corresponds for each compound to one row of Table A Table 105
Compounds of the formula IA, IB, IC, ID, IE, IF, IG, IH, II, IK, IL, IM, IN and IO in which $L_n$ is 2-chloro,4-fluoro, $R^2$ is methoxy and $R^1$ corresponds for each compound to one row of Table A Table 106
Compounds of the formula IA, IB, IC, ID, IE, IF, IG, IH, II, IK, IL, IM, IN and IO in which $L_n$ is 2,3-difluoro, $R^2$ is methoxy and $R^1$ corresponds for each compound to one row of Table A Table 107
Compounds of the formula IA, IB, IC, ID, IE, IF, IG, IH, II, IK, IL, IM, IN and IO in which $L_n$ is 2,5-difluoro, $R^2$ is methoxy and $R^1$ corresponds for each compound to one row of Table A Table 108
Compounds of the formula IA, IB, IC, ID, IE, IF, IG, IH, II, IK, IL, IM, IN and IO in which $L_n$ is 2,3,4-trifluoro, $R^2$ is methoxy and $R^1$ corresponds for each compound to one row of Table A Table 109
Compounds of the formula IA, IB, IC, ID, IE, IF, IG, IH, II, IK, IL, IM, IN and IO in which $L_n$ is 2-methyl, $R^2$ is methoxy and $R^1$ corresponds for each compound to one row of Table A Table 110
Compounds of the formula IA, IB, IC, ID, IE, IF, IG, IH, II, IK, IL, IM, IN and IO in which $L_n$ is 2,4-dimethyl, $R^2$ is methoxy and $R^1$ corresponds for each compound to one row of Table A Table 111
Compounds of the formula IA, IB, IC, ID, IE, IF, IG, IH, II, IK, IL, IM, IN and IO in which $L_n$ is 2-methyl,4-chloro, $R^2$ is methoxy and $R^1$ corresponds for each compound to one row of Table A Table 112
Compounds of the formula IA, IB, IC, ID, IE, IF, IG, IH, II, IK, IL, IM, IN and IO in which $L_n$ is 2-fluoro,4-methyl, $R^2$ is methoxy and $R^1$ corresponds for each compound to one row of Table A Table 113
Compounds of the formula IA, IB, IC, ID, IE, IF, IG, IH, II, IK, IL, IM, IN and IO in which $L_n$ is 2,6-dimethyl, $R^2$ is methoxy and $R^1$ corresponds for each compound to one row of Table A Table 114
Compounds of the formula IA, IB, IC, ID, IE, IF, IG, IH, II, IK, IL, IM, IN and IO in which $L_n$ is 2,4,6-trimethyl, $R^2$ is methoxy and $R^1$ corresponds for each compound to one row of Table A Table 115
Compounds of the formula IA, IB, IC, ID, IE, IF, IG, IH, II, IK, IL, IM, IN and IO in which $L_n$ is 2,6-difluoro,4-cyano, $R^2$ is methoxy and $R^1$ corresponds for each compound to one row of Table A Table 116
Compounds of the formula IA, IB, IC, ID, IE, IF, IG, IH, II, IK, IL, IM, IN and IO in which $L_n$ is 2,6-difluoro,4-methyl, $R^2$ is methoxy and $R^1$ corresponds for each compound to one row of Table A Table 117
Compounds of the formula IA, IB, IC, ID, IE, IF, IG, IH, II, IK, IL, IM, IN and IO in which $L_n$ is 2,6-difluoro,4-methoxycarbonyl, $R^2$ is methoxy and $R^1$ corresponds for each compound to one row of Table A Table 118
Compounds of the formula IA, IB, IC, ID, IE, IF, IG, IH, II, IK, IL, IM, IN and IO in which $L_n$ is 2-chloro,4-methoxy, $R^2$ is methoxy and $R^1$ corresponds for each compound to one row of Table A Table 119
Compounds of the formula IA, IB, IC, ID, IE, IF, IG, IH, II, IK, IL, IM, IN and IO in which $L_n$ is 2-chloro,4-methyl, $R^2$ is methoxy and $R^1$ corresponds for each compound to one row of Table A Table 120
Compounds of the formula IA, IB, IC, ID, IE, IF, IG, IH, II, IK, IL, IM, IN and IO in which $L_n$ is 2-chloro,4-methoxycarbonyl, $R^2$ is methoxy and $R^1$ corresponds for each compound to one row of Table A Table 121
Compounds of the formula IA, IB, IC, ID, IE, IF, IG, IH, II, IK, IL, IM, IN and IO in which $L_n$ is 2-chloro,4-bromo, $R^2$ is methoxy and $R^1$ corresponds for each compound to one row of Table A Table 122
Compounds of the formula IA, IB, IC, ID, IE, IF, IG, IH, II, IK, IL, IM, IN and IO in which $L_n$ is 2-chloro,4-cyano, $R^2$ is methoxy and $R^1$ corresponds for each compound to one row of Table A Table 123
Compounds of the formula IA, IB, IC, ID, IE, IF, IG, IH, II, IK, IL, IM, IN and IO in which $L_n$ is 2,6-difluoro,4-methoxy, $R^2$ is methoxy and $R^1$ corresponds for each compound to one row of Table A Table 124
Compounds of the formula IA, IB, IC, ID, IE, IF, IG, IH, II, IK, IL, IM, IN and IO in which $L_n$ is 2-fluoro,3-methyl, $R^2$ is methoxy and $R^1$ corresponds for each compound to one row of Table A Table 125
Compounds of the formula IA, IB, IC, ID, IE, IF, IG, IH, II, IK, IL, IM, IN and IO in which $L_n$ is 2,5-dimethyl, $R^2$ is methoxy and $R^1$ corresponds for each compound to one row of Table A Table 126
Compounds of the formula IA, IB, IC, ID, IE, IF, IG, IH, II, IK, IL, IM, IN and IO in which $L_n$ is 2-methyl,4-cyano, $R^2$ is methoxy and $R^1$ corresponds for each compound to one row of Table A Table 127
Compounds of the formula IA, IB, IC, ID, IE, IF, IG, IH, II, IK, IL, IM, IN and IO in which $L_n$ is 2-methyl,4-bromo, $R^2$ is methoxy and $R^1$ corresponds for each compound to one row of Table A Table 128
Compounds of the formula IA, IB, IC, ID, IE, IF, IG, IH, II, IK, IL, IM, IN and IO in which $L_n$ is 2-methyl,5-fluoro, $R^2$ is methoxy and $R^1$ corresponds for each compound to one row of Table A Table 129
Compounds of the formula IA, IB, IC, ID, IE, IF, IG, IH, II, IK, IL, IM, IN and IO in which $L_n$ is 2-methyl,4-methoxy, $R^2$ is methoxy and $R^1$ corresponds for each compound to one row of Table A Table 130
Compounds of the formula IA, IB, IC, ID, IE, IF, IG, IH, II, IK, IL, IM, IN and IO in which $L_n$ is 2-methyl,4-methoxycarbonyl, $R^2$ is methoxy and $R^1$ corresponds for each compound to one row of Table A Table 131
Compounds of the formula IA, IB, IC, ID, IE, IF, IG, IH, II, IK, IL, IM, IN and IO in which $L_n$ is 2,5-dimethyl,4-bromo, $R^2$ is methoxy and $R^1$ corresponds for each compound to one row of Table A Table 132
Compounds of the formula IA, IB, IC, ID, IE, IF, IG, IH, II, IK, IL, IM, IN and IO in which $L_n$ is 2-fluoro,4-bromo, $R^2$ is methoxy and $R^1$ corresponds for each compound to one row of Table A Table 133
Compounds of the formula IA, IB, IC, ID, IE, IF, IG, IH, II, IK, IL, IM, IN and IO in which $L_n$ is 2-fluoro,4-methoxy, $R^2$ is methoxy and $R^1$ corresponds for each compound to one row of Table A Table 134
Compounds of the formula IA, IB, IC, ID, IE, IF, IG, IH, II, IK, IL, IM, IN and IO in which $L_n$ is 2-fluoro,5-methyl, $R^2$ is methoxy and $R^1$ corresponds for each compound to one row of Table A Table 135
Compounds of the formula IA, IB, IC, ID, IE, IF, IG, IH, II, IK, IL, IM, IN and IO in which $L_n$ is pentafluoro, $R^2$ methoxy and $R^1$ corresponds for each compound to one row of Table A Table 136
Compounds of the formula IA, IB, IC, ID, IE, IF, IG, IH, II, IK, IL, IM, IN and IO in which $L_n$ is 2-fluoro,6-chloro, $R^2$ is cyano and $R^1$ corresponds for each compound to one row of Table A Table 137
Compounds of the formula IA, IB, IC, ID, IE,.IF, IG, IH, II, IK, IL, IM, IN and IO in which $L_n$ is 2,6-difluoro, $R^2$ is cyano and $R^1$ corresponds for each compound to one row of Table A Table 138
Compounds of the formula IA, IB, IC, ID, IE, IF, IG, IH, II, IK, IL, IM, IN and IO in which $L_n$ is 2,6-dichloro, $R^2$ is cyano and $R^1$ corresponds for each compound to one row of Table A Table 139
Compounds of the formula IA, IB, IC, ID, IE, IF, IG, IH, II, IK, IL, IM, IN and IO in which $L_n$ is 2-fluoro,6-methyl, $R^2$ is cyano and $R^1$ corresponds for each compound to one row of Table A Table 140
Compounds of the formula IA, IB, IC, ID, IE, IF, IG, IH, II, IK, IL, IM, IN and IO in which $L_n$ is 2,4,6-trifluoro, $R^2$ is cyano and $R^1$ corresponds for each compound to one row of Table A Table 141
Compounds of the formula IA, IB, IC, ID, IE, IF, IG, IH, II, IK, IL, IM, IN and IO in which $L_n$ is 2-methyl,4-fluoro, $R^2$ is cyano and $R^1$ corresponds for each compound to one row of Table A Table 142
Compounds of the formula IA, IB, IC, ID, IE, IF, IG, IH, II, IK, IL, IM, IN and IO in which $L_n$ is 2-fluoro,4-methoxycarbonyl, $R^2$ is cyano and $R^1$ corresponds for each compound to one row of Table A Table 143
Compounds of the formula IA, IB, IC, ID, IE, IF, IG, IH, II, IK, IL, IM, IN and IO in which $L_n$ is 2-fluoro,4-CN, $R^2$ is cyano and $R^1$ corresponds for each compound to one row of Table A Table 144
Compounds of the formula IA, IB, IC, ID, IE, IF, IG, IH, II, IK, IL, IM, IN and IO in which $L_n$ is 2,4,5-trifluoro, $R^2$ is cyano and $R^1$ corresponds for each compound to one row of Table A Table 145
Compounds of the formula IA, IB, IC, ID, IE, IF, IG, IH, II, IK, IL, IM, IN and IO in which $L_n$ is 2,4-dichloro, $R^2$ is cyano and $R^1$ corresponds for each compound to one row of Table A Table 146
Compounds of the formula IA, IB, IC, ID, IE, IF, IG, IH, II, IK, IL, IM, IN and IO in which $L_n$ is 2-chloro, $R^2$ is cyano and $R^1$ corresponds for each compound to one row of Table A Table 147
Compounds of the formula IA, IB, IC, ID, IE, IF, IG, IH, II, IK, IL, IM, IN and IO in which $L_n$ is 2-fluoro, $R^2$ is cyano and $R^1$ corresponds for each compound to one row of Table A Table 148
Compounds of the formula IA, IB, IC, ID, IE, IF, IG, IH, II, IK, IL, IM, IN and IO in which $L_n$ is 2,4-difluoro, $R^2$ is cyano and $R^1$ corresponds for each compound to one row of Table A Table 149
Compounds of the formula IA, IB, IC, ID, IE, IF, IG, IH, II, IK, IL, IM, IN and IO in which $L_n$ is 2-fluoro,4-chloro, $R^2$ is cyano and $R^1$ corresponds for each compound to one row of Table A Table 150
Compounds of the formula IA, IB, IC, ID, IE, IF, IG, IH, II, IK, IL, IM, IN and IO in which $L_n$ is 2-chloro,4-fluoro, $R^2$ is cyano and $R^1$ corresponds for each compound to one row of Table A Table 151
Compounds of the formula IA, IB, IC, ID, IE, IF, IG, IH, II, IK, IL, IM, IN and IO in which $L_n$ is 2,3-difluoro, $R^2$ is cyano and $R^1$ corresponds for each compound to one row of Table A Table 152
Compounds of the formula IA, IB, IC, ID, IE, IF, IG, IH, II, IK, IL, IM, IN and IO in which $L_n$ is 2,5-difluoro, $R^2$ is cyano and $R^1$ corresponds for each compound to one row of Table A Table 153
Compounds of the formula IA, IB, IC, ID, IE, IF, IG, IH, II, IK, IL, IM, IN and IO in which $L_n$ is 2,3,4-trifluoro, $R^2$ is cyano and $R^1$ corresponds for each compound to one row of Table A Table 154
Compounds of the formula IA, IB, IC, ID, IE, IF, IG, IH, II, IK, IL, IM, IN and IO in which $L_n$ is 2-methyl, $R^2$ is cyano and $R^1$ corresponds for each compound to one row of Table A Table 155
Compounds of the formula IA, IB, IC, ID, IE, IF, IG, IH, II, IK, IL, IM, IN and IO in which $L_n$ is 2,4-dimethyl, $R^2$ is cyano and $R^1$ corresponds for each compound to one row of Table A Table 156
Compounds of the formula IA, IB, IC, ID, IE, IF, IG, IH, II, IK, IL, IM, IN and IO in which $L_n$ is 2-methyl,4-chloro, $R^2$ is cyano and $R^1$ corresponds for each compound to one row of Table A Table 157
Compounds of the formula IA, IB, IC, ID, IE, IF, IG, IH, II, IK, IL, IM, IN and IO in which $L_n$ is 2-fluoro,4-methyl, $R^2$ is cyano and $R^1$ corresponds for each compound to one row of Table A Table 158
Compounds of the formula IA, IB, IC, ID, IE, IF, IG, IH, II, IK, IL, IM, IN and IO in which $L_n$ is 2,6-dimethyl, $R^2$ is cyano and $R^1$ corresponds for each compound to one row of Table A Table 159
Compounds of the formula IA, IB, IC, ID, IE, IF, IG, IH, II, IK, IL, IM, IN and IO in which $L_n$ is 2,4,6-trimethyl, $R^2$ is cyano and $R^1$ corresponds for each compound to one row of Table A Table 160
Compounds of the formula IA, IB, IC, ID, IE, IF, IG, IH, II, IK, IL, IM, IN and IO in which $L_n$ is 2,6-difluoro,4-cyano, $R^2$ is cyano and $R^1$ corresponds for each compound to one row of Table A Table 161
Compounds of the formula IA, IB, IC, ID, IE, IF, IG, IH, II, IK, IL, IM, IN and IO in which $L_n$ is 2,6-difluoro,4-methyl, $R^2$ is cyano and $R^1$ corresponds for each compound to one row of Table A Table 162
Compounds of the formula IA, IB, IC, ID, IE, IF, IG, IH, II, IK, IL, IM, IN and IO in which $L_n$ is 2,6-difluoro,4-methoxycarbonyl, $R^2$ is cyano and $R^1$ corresponds for each compound to one row of Table A Table 163
Compounds of the formula IA, IB, IC, ID, IE, IF, IG, IH, II, IK, IL, IM, IN and IO in which $L_n$ is 2-chloro,4-methoxy, $R^2$ is cyano and $R^1$ corresponds for each compound to one row of Table A Table 164
Compounds of the formula IA, IB, IC, ID, IE, IF, IG, IH, II, IK, IL, IM, IN and IO in which $L_n$ is 2-chloro,4-methyl, $R^2$ is cyano and $R^1$ corresponds for each compound to one row of Table A Table 165
Compounds of the formula IA, IB, IC, ID, IE, IF, IG, IH, II, IK, IL, IM, IN and IO in which $L_n$ is 2-chloro,4-methoxycarbonyl, $R^2$ is cyano and $R^1$ corresponds for each compound to one row of Table A Table 166
Compounds of the formula IA, IB, IC, ID, IE, IF, IG, IH, II, IK, IL, IM, IN and IO in which $L_n$ is 2-chloro,4-bromo, $R^2$ is cyano and $R^1$ corresponds for each compound to one row of Table A Table 167
Compounds of the formula IA, IB, IC, ID, IE, IF, IG, IH, II, IK, IL, IM, IN and IO in which $L_n$ is 2-chloro,4-cyano, $R^2$ is cyano and $R^1$ corresponds for each compound to one row of Table A Table 168
Compounds of the formula IA, IB, IC, ID, IE, IF, IG, IH, II, IK, IL, IM, IN and IO in which $L_n$ is 2,6-difluoro,4-methoxy, $R^2$ is cyano and $R^1$ corresponds for each compound to one row of Table A Table 169
Compounds of the formula IA, IB, IC, ID, IE, IF, IG, IH, II, IK, IL, IM, IN and IO in which $L_n$ is 2-fluoro,3-methyl, $R^2$ is cyano and $R^1$ corresponds for each compound to one row of Table A Table 170
Compounds of the formula IA, IB, IC, ID, IE, IF, IG, IH, II, IK, IL, IM, IN and IO in which $L_n$ is 2,5-dimethyl, $R^2$ is cyano and $R^1$ corresponds for each compound to one row of Table A Table 171
Compounds of the formula IA, IB, IC, ID, IE, IF, IG, IH, II, IK, IL, IM, IN and IO in which $L_n$ is 2-methyl,4-cyano, $R^2$ is cyano and $R^1$ corresponds for each compound to one row of Table A Table 172
Compounds of the formula IA, IB, IC, ID, IE, IF, IG, IH, II, IK, IL, IM, IN and IO in which $L_n$ is 2-methyl,4-bromo, $R^2$ is cyano and $R^1$ corresponds for each compound to one row of Table A Table 173
Compounds of the formula IA, IB, IC, ID, IE, IF, IG, IH, II, IK, IL, IM, IN and IO in which $L_n$ is 2-methyl,5-fluoro, $R^2$ is cyano and $R^1$ corresponds for each compound to one row of Table A Table 174
Compounds of the formula IA, IB, IC, ID, IE, IF, IG, IH, II, IK, IL, IM, IN and IO in which $L_n$ is 2-methyl,4-methoxy, $R^2$ is cyano and $R^1$ corresponds for each compound to one row of Table A Table 175
Compounds of the formula IA, IB, IC, ID, IE, IF, IG, IH, II, IK, IL, IM, IN and IO in which $L_n$ is 2-methyl,4-methoxycarbonyl, $R^2$ is cyano and $R^1$ corresponds to one row of Table A Table 176
Compounds of the formula IA, IB, IC, ID, IE, IF, IG, IH, II, IK, IL, IM, IN and IO in which $L_n$ is 2,5-dimethyl,4-bromo, $R^2$ is cyano and $R^1$ corresponds for each compound to one row of Table A Table 177
Compounds of the formula IA, IB, IC, ID, IE, IF, IG, IH, II, IK, IL, IM, IN and IO in which $L_n$ is 2-fluoro,4-bromo, $R^2$ is cyano and $R^1$ corresponds for each compound to one row of Table A Table 178
Compounds of the formula IA, IB, IC, ID, IE, IF, IG, IH, II, IK, IL, IM, IN and IO in which $L_n$ is 2-fluoro,4-methoxy, $R^2$ is cyano and $R^1$ corresponds for each compound to one row of Table A Table 179
Compounds of the formula IA, IB, IC, ID, IE, IF, IG, IH, II, IK, IL, IM, IN and IO in which $L_n$ is 2-fluoro,5-methyl, $R^2$ is cyano and $R^1$ corresponds for each compound to one row of Table A Table 180
Compounds of the formula IA, IB, IC, ID, IE, IF, IG, IH, II, IK, IL, IM, IN and IO in which $L_n$ is pentafluoro, $R^2$ is cyano and $R^1$ corresponds for each compound to one row of Table A

TABLE A

| No. | $R^1$ |
|---|---|
| A-1 | $CH_3$ |
| A-2 | $CH_2CH_3$ |
| A-3 | $CH_2CH_2CH_3$ |
| A-4 | $CH(CH_3)_2$ |
| A-5 | $CH_2CH(CH_3)_2$ |
| A-6 | $(\pm)CH(CH_3)CH_2CH_3$ |
| A-7 | $(R)CH(CH_3)CH_2CH_3$ |
| A-8 | $(S)CH(CH_3)CH_2CH_3$ |
| A-9 | $(CH_2)_3CH_3$ |
| A-10 | $C(CH_3)_3$ |
| A-11 | $(CH_2)_4CH_3$ |
| A-12 | $CH(CH_2CH_3)_2$ |
| A-13 | $CH_2CH_2CH(CH_3)_2$ |
| A-14 | $(\pm)CH(CH_3)(CH_2)_2CH_3$ |
| A-15 | $(R)CH(CH_3)(CH_2)_2CH_3$ |
| A-16 | $(S)CH(CH_3)(CH_2)_2CH_3$ |
| A-17 | $(\pm)CH_2CH(CH_3)CH_2CH_3$ |
| A-18 | $(R)CH_2CH(CH_3)CH_2CH_3$ |
| A-19 | $(S)CH_2CH(CH_3)CH_2CH_3$ |
| A-20 | $(\pm)CH(CH_3)CH(CH_3)_2$ |
| A-21 | $(R)CH(CH_3)CH(CH_3)_2$ |
| A-22 | $(S)CH(CH_3)CH(CH_3)_2$ |
| A-23 | $(CH_2)_5CH_3$ |
| A-24 | $(\pm,\pm)CH(CH_3)CH(CH_3)CH_2CH_3$ |
| A-25 | $(\pm,R)CH(CH_3)CH(CH_3)CH_2CH_3$ |
| A-26 | $(\pm,S)CH(CH_3)CH(CH_3)CH_2CH_3$ |
| A-27 | $(\pm)CH_2CH(CH_3)CF_3$ |
| A-28 | $(R)CH_2CH(CH_3)CF_3$ |
| A-29 | $(S)CH_2CH(CH_3)CF_3$ |
| A-30 | $(\pm)CH_2CH(CF_3)CH_2CH_3$ |
| A-31 | $(R)CH_2CH(CF_3)CH_2CH_3$ |
| A-32 | $(S)CH_2CH(CF_3)CH_2CH_3$ |
| A-33 | $(\pm,\pm)CH(CH_3)CH(CH_3)CF_3$ |
| A-34 | $(\pm,R)CH(CH_3)CH(CH_3)CF_3$ |
| A-35 | $(\pm,S)CH(CH_3)CH(CH_3)CF_3$ |
| A-36 | $(\pm,\pm)CH(CH_3)CH(CF_3)CH_2CH_3$ |
| A-37 | $(\pm,R)CH(CH_3)CH(CF_3)CH_2CH_3$ |
| A-38 | $(\pm,S)CH(CH_3)CH(CF_3)CH_2CH_3$ |
| A-39 | $CF_3$ |
| A-40 | $CF_2CF_3$ |
| A-41 | $CF_2CF_2CF_3$ |
| A-42 | $c-C_3H_5$ |
| A-43 | $(1-CH_3)-c-C_3H_4$ |
| A-44 | $c-C_5H_9$ |
| A-45 | $c-C_6H_{11}$ |
| A-46 | $(4-CH_3)-c-C_6H_{10}$ |
| A-47 | $CH_2C(CH_3)=CH_2$ |
| A-48 | $CH_2CH_2C(CH_3)=CH_2$ |
| A-49 | $CH_2-C(CH_3)_3$ |
| A-50 | $CH_2-Si(CH_3)_3$ |
| A-51 | $n-C_6H_{13}$ |
| A-52 | $(CH_2)_3-CH(CH_3)_2$ |
| A-53 | $(CH_2)_2-CH(CH_3)-C_2H_5$ |
| A-54 | $CH_2-CH(CH_3)-n-C_3H_7$ |
| A-55 | $CH(CH_3)-n-C_4H_9$ |
| A-56 | $CH_2-CH(C_2H_5)_2$ |
| A-57 | $CH(C_2H_5)-n-C_3H_7$ |
| A-58 | $CH_2-c-C_5H_9$ |
| A-59 | $CH_2-CH(CH_3)-CH(CH_3)_2$ |
| A-60 | $CH(CH_3)-CH_2CH(CH_3)_2$ |
| A-61 | $CH(CH_3)-CH(CH_3)-C_2H_5$ |
| A-62 | $CH(CH_3)-C(CH_3)_3$ |
| A-63 | $(CH_2)_2-C(CH_3)_3$ |
| A-64 | $CH_2-C(CH_3)_2-C_2H_5$ |
| A-65 | $2-CH_3-c-C_5H_8$ |
| A-66 | $3-CH_3-c-C_5H_8$ |
| A-67 | $C(CH_3)_2-n-C_3H_7$ |
| A-68 | $(CH_2)_6-CH_3$ |
| A-69 | $(CH_2)_4-CH(CH_3)_2$ |
| A-70 | $(CH_2)_3-CH(CH_3)-C_2H_5$ |
| A-71 | $(CH_2)_2-CH(CH_3)-n-C_3H_7$ |
| A-72 | $CH_2-CH(CH_3)-n-C_4H_9$ |
| A-73 | $CH(CH_3)-n-C_5H_{11}$ |
| A-74 | $(CH_2)_3C(CH_3)_3$ |
| A-75 | $(CH_2)_2CH(CH_3)-CH(CH_3)_2$ |
| A-76 | $(CH_2)CH(CH_3)-CH_2CH(CH_3)_2$ |
| A-77 | $CH(CH_3)(CH_2)_2-CH(CH_3)_2$ |
| A-78 | $(CH_2)_2C(CH_3)_2C_2H_5$ |
| A-79 | $CH_2CH(CH_3)CH(CH_3)C_2H_5$ |
| A-80 | $CH(CH_3)CH_2CH(CH_3)C_2H_5$ |
| A-81 | $CH_2C(CH_3)_2-n-C_3H_7$ |
| A-82 | $CH(CH_3)CH(CH_3)-n-C_3H_7$ |
| A-83 | $C(CH_3)_2-n-C_4H_9$ |
| A-84 | $(CH_2)_2CH(C_2H_5)_2$ |
| A-85 | $CH_2CH(C_2H_5)-n-C_3H_7$ |
| A-86 | $CH(C_2H_5)-n-C_4H_9$ |
| A-87 | $CH_2CH(CH_3)C(CH_3)_3$ |

TABLE A-continued

| No. | R¹ |
|---|---|
| A-88 | CH(CH$_3$)CH$_2$C(CH$_3$)$_3$ |
| A-89 | CH$_2$C(CH$_3$)$_2$CH(CH$_3$)$_2$ |
| A-90 | CH$_2$CH(C$_2$H$_5$)CH(CH$_3$)$_2$ |
| A-91 | CH(CH$_3$)CH(CH$_3$)CH(CH$_3$)$_2$ |
| A-92 | C(CH$_3$)$_2$CH$_2$CH(CH$_3$)$_2$ |
| A-93 | C(C$_2$H$_5$)$_2$CH$_2$CH(CH$_3$)$_2$ |
| A-94 | CH(CH$_3$)C(CH$_3$)$_2$C$_2$H$_5$ |
| A-95 | CH(CH$_3$)CH(C$_2$H$_5$)$_2$ |
| A-96 | C(CH$_3$)$_2$CH(CH$_3$)C$_2$H$_5$ |
| A-97 | CH(C$_2$H$_5$)CH(CH$_3$)C$_2$H$_5$ |
| A-98 | C(CH$_3$)(C$_2$H$_5$)-n-C$_3$H$_7$ |
| A-99 | CH(n-C$_3$H$_7$)$_2$ |
| A-100 | CH(n-C$_3$H$_7$)CH(CH$_3$)$_2$ |
| A-101 | C(CH$_3$)$_2$C(CH$_3$)$_3$ |
| A-102 | C(CH$_3$)(C$_2$H$_5$)—CH(CH$_3$)$_2$ |
| A-103 | C(C$_2$H$_5$)$_3$ |
| A-104 | (3-CH$_3$)-c-C$_6$H$_{10}$ |
| A-105 | (2-CH$_3$)-c-C$_6$H$_{10}$ |
| A-106 | n-C$_8$H$_{17}$ |
| A-107 | CH$_2$C(=NO—CH$_3$)CH$_3$ |
| A-108 | CH$_2$C(=NO—C$_2$H$_5$)CH$_3$ |
| A-109 | CH$_2$C(=NO-n-C$_3$H$_7$)CH$_3$ |
| A-110 | CH$_2$C(=NO-i-C$_3$H$_7$)CH$_3$ |
| A-111 | CH(CH$_3$)C(=NOCH$_3$)CH$_3$ |
| A-112 | CH(CH$_3$)C(=NOC$_2$H$_5$)CH$_3$ |
| A-113 | CH(CH$_3$)C(=NO-n-C$_3$H$_7$)CH$_3$ |
| A-114 | CH(CH$_3$)C(=NO-i-C$_3$H$_7$)CH$_3$ |
| A-115 | C(=NOCH$_3$)C(=NOCH$_3$)CH$_3$ |
| A-116 | C(=NOCH$_3$)C(=NOC$_2$H$_5$)CH$_3$ |
| A-117 | C(=NOCH$_3$)C(=NO-n-C$_3$H$_7$)CH$_3$ |
| A-118 | C(=NOCH$_3$)C(=NO-i-C$_3$H$_7$)CH$_3$ |
| A-119 | C(=NOC$_2$H$_5$)C(=NOCH$_3$)CH$_3$ |
| A-120 | C(=NOC$_2$H$_5$)C(=NOC$_2$H$_5$)CH$_3$ |
| A-121 | C(=NOC$_2$H$_5$)C(=NO-n-C$_3$H$_7$)CH$_3$ |
| A-122 | C(=NOC$_2$H$_5$)C(=NO-i-C$_3$H$_7$)CH$_3$ |
| A-123 | CH$_2$C(=NO—CH$_3$)C$_2$H$_5$ |
| A-124 | CH$_2$C(=NO—C$_2$H$_5$)C$_2$H$_5$ |
| A-125 | CH$_2$C(=NO-n-C$_3$H$_7$)C$_2$H$_5$ |
| A-126 | CH$_2$C(=NO-i-C$_3$H$_7$)C$_2$H$_5$ |
| A-127 | CH(CH$_3$)C(=NOCH$_3$)C$_2$H$_5$ |
| A-128 | CH(CH$_3$)C(=NOC$_2$H$_5$)C$_2$H$_5$ |
| A-129 | CH(CH$_3$)C(=NO-n-C$_3$H$_7$)C$_2$H$_5$ |
| A-130 | CH(CH$_3$)C(=NO-n-C$_3$H$_7$)C$_2$H$_5$ |
| A-131 | C(=NOCH$_3$)C(=NOCH$_3$)C$_2$H$_5$ |
| A-132 | C(=NOCH$_3$)C(=NOC$_2$H$_5$)C$_2$H$_5$ |
| A-133 | C(=NOCH$_3$)C(=NO-n-C$_3$H$_7$)C$_2$H$_5$ |
| A-134 | C(=NOCH$_3$)C(=NO-i-C$_3$H$_7$)C$_2$H$_5$ |
| A-135 | C(=NOC$_2$H$_5$)C(=NOCH$_3$)C$_2$H$_5$ |
| A-136 | C(=NOC$_2$H$_5$)C(=NOC$_2$H$_5$)C$_2$H$_5$ |
| A-137 | C(=NOC$_2$H$_5$)C(=NO-n-C$_3$H$_7$)C$_2$H$_5$ |
| A-138 | C(=NOC$_2$H$_5$)C(=NO-i-C$_3$H$_7$)C$_2$H$_5$ |
| A-139 | CH=CH—CH$_2$CH$_3$ |
| A-140 | CH$_2$—CH=CH—CH$_3$ |
| A-141 | CH$_2$—CH$_2$—CH=CH$_2$ |
| A-142 | C(CH$_3$)$_2$CH$_2$CH$_3$ |
| A-143 | CH=C(CH$_3$)$_2$ |
| A-144 | C(=CH$_2$)—CH$_2$CH$_3$ |
| A-145 | C(CH$_3$)=CH—CH$_3$ |
| A-146 | CH(CH$_3$)CH=CH$_2$ |
| A-147 | CH=CH-n-C$_3$H$_7$ |
| A-148 | CH$_2$—CH=CH—C$_2$H$_5$ |
| A-149 | (CH$_2$)$_2$—CH=CH—CH$_3$ |
| A-150 | (CH$_2$)$_3$—CH=CH$_2$ |
| A-151 | CH=CH—CH(CH$_3$)$_2$ |
| A-152 | CH$_2$—CH=C(CH$_3$)$_2$ |
| A-153 | (CH$_2$)$_2$—C(CH$_3$)=CH$_2$ |
| A-154 | CH=C(CH$_3$)—C$_2$H$_5$ |
| A-155 | CH$_2$—C(=CH$_2$)—C$_2$H$_5$ |
| A-156 | CH$_2$—C(CH$_3$)=CH—CH$_3$ |
| A-157 | CH$_2$—CH(CH$_3$)—CH=CH$_2$ |
| A-158 | C(=CH$_2$)—CH$_2$—CH$_2$—CH$_3$ |
| A-159 | C(CH$_3$)—CH=CH—CH$_3$ |
| A-160 | CH(CH$_3$)—CH=CH—CH$_3$ |
| A-161 | CH(CH$_3$)—CH$_2$—CH=CH$_2$ |
| A-162 | C(=CH$_2$)CH(CH$_3$)$_2$ |
| A-163 | C(CH$_3$)=C(CH$_3$)$_2$ |
| A-164 | CH(CH$_3$)—C(=CH$_2$)—CH$_3$ |
| A-165 | C(CH$_3$)$_2$—CH=CH$_2$ |
| A-166 | C(C$_2$H$_5$)=CH—CH$_3$ |
| A-167 | CH(C$_2$H$_5$)—CH=CH$_2$ |
| A-168 | CH=CH—CH$_2$—CH$_2$—CH$_2$—CH$_3$ |
| A-169 | CH$_2$—CH=CH—CH$_2$—CH$_2$—CH$_3$ |
| A-170 | CH$_2$—CH$_2$—CH=CH—CH$_2$—CH$_3$ |
| A-171 | CH$_2$—CH$_2$—CH$_2$—CH=CH—CH$_3$ |
| A-172 | CH$_2$—CH$_2$—CH$_2$—CH$_2$—CH=CH$_2$ |
| A-173 | CH=CH—CH$_2$—CH(CH$_3$)CH$_3$ |
| A-174 | CH$_2$—CH=CH—CH(CH$_3$)CH$_3$ |
| A-175 | CH$_2$—CH$_2$—CH=C(CH$_3$)CH$_3$ |
| A-176 | CH$_2$—CH$_2$—CH$_2$—C(CH$_3$)=CH$_2$ |
| A-177 | CH=CH—CH(CH$_3$)—CH$_2$—CH$_3$ |
| A-178 | CH$_2$—CH=C(CH$_3$)—CH$_2$—CH$_3$ |
| A-179 | CH$_2$—CH$_2$—C(=CH$_2$)—CH$_2$—CH$_3$ |
| A-180 | CH$_2$—CH$_2$—C(CH$_3$)=CH—CH$_3$ |
| A-181 | CH$_2$—CH$_2$—CH(CH$_3$)—CH=CH$_2$ |
| A-182 | CH=C(CH$_3$)—CH$_2$—CH$_2$—CH$_3$ |
| A-183 | CH$_2$—C(=CH$_2$)—CH$_2$—CH$_2$—CH$_3$ |
| A-184 | CH$_2$—C(CH$_3$)=CH—CH$_2$—CH$_3$ |
| A-185 | CH$_2$—CH(CH$_3$)—CH=CH—CH$_3$ |
| A-186 | CH$_2$—CH(CH$_3$)—CH$_2$—CH=CH$_2$ |
| A-187 | C(=CH$_2$)—CH$_2$—CH$_2$—CH$_2$—CH$_3$ |
| A-188 | C(CH$_3$)=CH—CH$_2$—CH$_2$—CH$_3$ |
| A-189 | CH(CH$_3$)—CH=CH—CH$_2$—CH$_3$ |
| A-190 | CH(CH$_3$)—CH$_2$—CH=CH—CH$_3$ |
| A-191 | CH(CH$_3$)—CH$_2$—CH$_2$—CH=CH$_2$ |
| A-192 | CH=CH—C(CH$_3$)$_3$ |
| A-193 | CH=C(CH$_3$)—CH(CH$_3$)—CH$_3$ |
| A-194 | CH$_2$—C(=CH$_2$)—CH(CH$_3$)—CH$_3$ |
| A-195 | CH$_2$—C(CH$_3$)=C(CH$_3$)—CH$_3$ |
| A-196 | CH$_2$—CH(CH$_3$)—C(=CH$_2$)—CH$_3$ |
| A-197 | C(=CH$_2$)—CH$_2$—CH(CH$_3$)—CH$_3$ |
| A-198 | C(CH$_3$)=CH—CH(CH$_3$)—CH$_3$ |
| A-199 | CH(CH$_3$)—CH=C(CH$_3$)—CH$_3$ |
| A-200 | CH(CH$_3$)—CH$_2$—C(=CH$_2$)—CH$_3$ |
| A-201 | CH=C(CH$_2$—CH$_3$)—CH$_2$—CH$_3$ |
| A-202 | CH$_2$—C(=CH—CH$_3$)—CH$_2$—CH$_3$ |
| A-203 | CH$_2$—CH(CH$_3$)—CH$_2$—CH$_2$—CH$_3$ |
| A-204 | C(=CH—CH$_3$)—CH$_2$—CH$_2$—CH$_3$ |
| A-205 | CH(CH=CH$_2$)—CH$_2$—CH$_2$—CH$_3$ |
| A-206 | C(CH$_2$—CH$_3$)=CH—CH$_2$—CH$_3$ |
| A-207 | CH(CH$_2$—CH$_3$)—CH$_2$—CH=CH$_2$ |
| A-208 | CH(CH$_2$—CH$_3$)—CH$_2$—CH=CH$_2$ |
| A-209 | CH$_2$—C(CH$_3$)$_2$—CH=CH$_2$ |
| A-210 | C(=CH$_2$)—CH(CH$_3$)—CH$_2$—CH$_3$ |
| A-211 | C(CH$_3$)=C(CH$_3$)—CH$_2$—CH$_3$ |
| A-212 | CH(CH$_3$)—C(=CH$_2$)—CH$_2$—CH$_3$ |
| A-213 | CH(CH$_3$)—C(CH$_3$)=CH—CH$_3$ |
| A-214 | CH(CH$_3$)—CH(CH$_3$)—CH=CH$_2$ |
| A-215 | C(CH$_3$)$_2$—CH=CH—CH$_3$ |
| A-216 | C(CH$_3$)$_2$—CH$_2$—CH=CH$_2$ |
| A-217 | C(=CH$_2$)—C(CH$_3$)$_3$ |
| A-218 | C(=CH—CH$_3$)—CH(CH$_3$)—CH$_3$ |
| A-219 | CH(CH=CH$_2$)—CH(CH$_3$)—CH$_3$ |
| A-220 | C(CH$_3$)=C(CH$_3$)—CH$_3$ |
| A-221 | CH(CH$_2$—CH$_3$)—C(=CH$_2$)—CH$_3$ |
| A-222 | C(CH$_3$)$_2$—C(=CH$_2$)—CH$_3$ |
| A-223 | C(CH$_3$)(CH=CH$_2$)—CH$_2$—CH$_3$ |
| A-224 | C(CH$_3$)(CH$_2$CH$_3$)—CH$_2$—CH$_2$—CH$_3$ |
| A-225 | CH(CH$_2$CH$_3$)—CH(CH$_3$)—CH$_2$—CH$_3$ |
| A-226 | CH(CH$_2$CH$_3$)—CH$_2$—CH(CH$_3$)—CH$_3$ |
| A-227 | C(CH$_3$)$_2$—C(CH$_3$)$_3$ |
| A-228 | C(CH$_3$)$_2$—C(CH$_3$)$_3$ |
| A-229 | C(CH$_3$)(CH$_2$—CH$_3$)—CH(CH$_3$)$_2$ |
| A-230 | CH(CH(CH$_3$)$_2$)—CH(CH$_3$)$_2$ |
| A-231 | CH=CH—CH$_2$—CH$_2$—CH$_2$—CH$_2$—CH$_3$ |
| A-232 | CH$_2$—CH=CH—CH$_2$—CH$_2$—CH$_2$—CH$_3$ |
| A-233 | CH$_2$—CH$_2$—CH=CH—CH$_2$—CH$_2$—CH$_3$ |
| A-234 | CH$_2$—CH$_2$—CH$_2$—CH=CH—CH$_2$—CH$_3$ |
| A-235 | CH$_2$—CH$_2$—CH$_2$—CH$_2$—CH=CH—CH$_3$ |
| A-236 | CH$_2$—CH$_2$—CH$_2$—CH$_2$—CH$_2$—CH=CH$_2$ |
| A-237 | CH=CH—CH$_2$—CH$_2$—CH(CH$_3$)—CH$_3$ |
| A-238 | CH$_2$—CH=CH—CH$_2$—CH(CH$_3$)—CH$_3$ |
| A-239 | CH$_2$—CH$_2$—CH=CH—CH(CH$_3$)—CH$_3$ |
| A-240 | CH$_2$—CH$_2$—CH$_2$—CH=C(CH$_3$)—CH$_3$ |
| A-241 | CH$_2$—CH$_2$—CH$_2$—CH$_2$—C(=CH$_2$)—CH$_3$ |

TABLE A-continued

| No. | R¹ |
|---|---|
| A-242 | CH=CH—CH₂—CH(CH₃)—CH₂—CH₃ |
| A-243 | CH₂—CH=CH—CH(CH₃)—CH₂—CH₃ |
| A-244 | CH₂—CH₂—CH=C(CH₃)—CH₂—CH₃ |
| A-245 | CH₂—CH₂—CH₂—C(=CH₂)—CH₂—CH₃ |
| A-246 | CH₂—CH₂—CH₂—C(CH₃)=CH—CH₃ |
| A-247 | CH₂—CH₂—CH₂—CH(CH₃)—CH=CH₂ |
| A-248 | CH=CH—CH(CH₃)—CH₂—CH₂—CH₃ |
| A-249 | CH₂—CH=C(CH₃)—CH₂—CH₂—CH₃ |
| A-250 | CH₂—CH₂—C(=CH₂)—CH₂—CH₂—CH₃ |
| A-251 | CH₂—CH₂—C(CH₃)=CH—CH₂—CH₃ |
| A-252 | CH₂—CH₂—CH(CH₃)—CH=CH—CH₃ |
| A-253 | CH₂—CH₂—CH(CH₃)—CH₂—CH=CH₂ |
| A-254 | CH=C(CH₃)—CH₂—CH₂—CH₂—CH₃ |
| A-255 | CH₂—C(=CH₂)—CH₂—CH₂—CH₂—CH₃ |
| A-256 | CH₂—C(CH₃)=CH—CH₂—CH₂—CH₃ |
| A-257 | CH₂—CH(CH₃)—CH=CH—CH₂—CH₃ |
| A-258 | CH₂—CH(CH₃)—CH₂—CH=CH—CH₃ |
| A-259 | CH₂—CH(CH₃)—CH₂—CH₂—CH=CH₂ |
| A-260 | C(=CH₂)—CH₂—CH₂—CH₂—CH₂—CH₃ |
| A-261 | C(CH₃)=CH—CH₂—CH₂—CH₂—CH₃ |
| A-262 | CH(CH₃)—CH=CH—CH₂—CH₂—CH₃ |
| A-263 | CH(CH₃)—CH₂—CH=CH—CH₂—CH₃ |
| A-264 | CH(CH₃)—CH₂—CH₂—CH=CH—CH₃ |
| A-265 | CH(CH₃)—CH₂—CH₂—CH₂—CH=CH₂ |
| A-266 | CH=CH—CH₂—C(CH₃)₃ |
| A-267 | CH₂—CH=CH—C(CH₃)₃ |
| A-268 | CH=CH—CH(CH₃)—CH(CH₃)₂ |
| A-269 | CH₂—CH=C(CH₃)—CH(CH₃)₂ |
| A-270 | CH₂—CH₂—C(=CH₂)—CH(CH₃)₂ |
| A-271 | CH₂—CH₂—C(CH₃)=C(CH₃)₂ |
| A-272 | CH₂—CH₂—CH(CH₃)—C(=CH₂)—CH₃ |
| A-273 | CH=C(CH₃)—CH₂—CH(CH₃)₂ |
| A-274 | CH₂—C(=CH₂)—CH₂—CH(CH₃)₂ |
| A-275 | CH₂—C(CH₃)=CH—CH(CH₃)₂ |
| A-276 | CH₂—CH(CH₃)—CH=C(CH₃)₂ |
| A-277 | CH₂—CH(CH₃)—CH₂—C(=CH₂)—CH₃ |
| A-278 | C(=CH₂)—CH₂—CH₂—CH(CH₃)₂ |
| A-279 | C(CH₃)=CH—CH₂—CH(CH₃)₂ |
| A-280 | CH(CH₃)—CH=CH—CH(CH₃)₂ |
| A-281 | CH(CH₃)—CH₂—CH=C(CH₃)₂ |
| A-282 | CH(CH₃)—CH₂—CH₂—C(=CH₂)—CH₃ |
| A-283 | CH=CH—C(CH₃)₂—CH₂—CH₃ |
| A-284 | CH₂—CH₂—C(CH₃)₂—CH=CH₂ |
| A-285 | CH=C(CH₃)—CH(CH₃)—CH₂—CH₃ |
| A-286 | CH₂—C(=CH₂)—CH(CH₃)—CH₂—CH₃ |
| A-287 | CH₂—C(CH₃)=C(CH₃)—CH₂—CH₃ |
| A-288 | CH₂—CH(CH₃)—C(=CH₂)—CH₂—CH₃ |
| A-289 | CH₂—CH(CH₃)—C(CH₃)=CH—CH₃ |
| A-290 | CH₂—CH(CH₃)—CH(CH₃)—CH=CH₂ |
| A-291 | C(=CH₂)—CH₂—CH(CH₃)—CH₂—CH₃ |
| A-292 | C(CH₃)=CH—CH(CH₃)—CH₂—CH₃ |
| A-293 | CH(CH₃)—CH=C(CH₃)—CH₂—CH₃ |
| A-294 | CH(CH₃)—CH₂—C(=CH₂)—CH₂—CH₃ |
| A-295 | CH(CH₃)—CH₂—C(CH₃)=CH—CH₃ |
| A-296 | CH(CH₃)—CH₂—CH(CH₃)—CH=CH₂ |
| A-297 | CH₂—C(CH₃)₂—CH=CH—CH₃ |
| A-298 | CH₂—C(CH₃)₂—CH₂—CH=CH₂ |
| A-299 | C(=CH₂)—CH(CH₃)—CH₂—CH₂—CH₃ |
| A-300 | C(CH₃)=C(CH₃)—CH₂—CH₂—CH₃ |
| A-301 | CH(CH₃)—C(=CH₂)—CH₂—CH₂—CH₃ |
| A-302 | CH(CH₃)—C(CH₃)=CH—CH₂—CH₃ |
| A-303 | CH(CH₃)—CH(CH₃)—CH=CH—CH₃ |
| A-304 | CH(CH₃)—CH(CH₃)—CH₂—CH=CH₂ |
| A-305 | C(CH₃)₂—CH=CH—CH₂—CH₃ |
| A-306 | C(CH₃)₂—CH₂—CH=CH—CH₃ |
| A-307 | C(CH₃)₂—CH₂—CH₂—CH=CH₂ |
| A-308 | CH=CH—CH(CH₂—CH₃)—CH₂—CH₃ |
| A-309 | CH₂—CH=C(CH₂—CH₃)—CH₂—CH₃ |
| A-310 | CH₂—CH₂—C(=CH—CH₃)—CH₂—CH₃ |
| A-311 | CH₂—CH₂—CH(CH=CH₂)—CH₂—CH₃ |
| A-312 | CH=C(CH₂—CH₃)—CH₂—CH₂—CH₃ |
| A-313 | CH₂—C(=CH—CH₃)—CH₂—CH₂—CH₃ |
| A-314 | CH₂—CH(CH=CH₂)—CH₂—CH₂—CH₃ |
| A-315 | CH₂—C(CH₂—CH₃)=CH—CH₂—CH₃ |
| A-316 | CH₂—CH(CH₂—CH₃)—CH=CH—CH₃ |
| A-317 | CH₂—CH(CH₂—CH₃)—CH₂—CH=CH₂ |
| A-318 | C(=CH—CH₃)—CH₂—CH₂—CH₂—CH₃ |
| A-319 | CH(CH=CH₂)—CH₂—CH₂—CH₂—CH₃ |
| A-320 | C(CH₂—CH₃)=CH—CH₂—CH₂—CH₃ |
| A-321 | CH(CH₂—CH₃)—CH=CH—CH₂—CH₃ |
| A-322 | CH(CH₂—CH₃)—CH₂—CH=CH—CH₃ |
| A-323 | CH(CH₂—CH₃)—CH₂—CH₂—CH=CH₂ |
| A-324 | C(=CH—CH₃)—CH₂—CH₂—CH₂—CH₃ |
| A-325 | C(CH=CH—CH₃)—CH₂—CH₂—CH₃ |
| A-326 | C(CH₂—CH=CH₂)—CH₂—CH₂—CH₃ |
| A-327 | CH=C(CH₃)—C(CH₃)₃ |
| A-328 | CH₂—C(=CH₂)—C(CH₃)₃ |
| A-329 | CH₂—C(CH₃)₂—CH(=CH₂)—CH₃ |
| A-330 | C(=CH₂)—CH(CH₃)—CH(CH₃)—CH₃ |
| A-331 | C(CH₃)=C(CH₃)—CH(CH₃)—CH₃ |
| A-332 | CH(CH₃)—C(=CH₂)—CH(CH₃)—CH₃ |
| A-333 | CH(CH₃)—C(CH₃)=C(CH₃)—CH₃ |
| A-334 | CH(CH₃)—CH(CH₃)—C(=CH₂)—CH₃ |
| A-335 | C(CH₃)₂—CH=C(CH₃)—CH₃ |
| A-336 | C(CH₃)₂—CH₂—C(=CH₂)—CH₃ |
| A-337 | C(CH₃)₂—C(=CH₂)—CH₂—CH₃ |
| A-338 | C(CH₃)₂—C(CH₃)=CH—CH₃ |
| A-339 | C(CH₃)₂—CH(CH₃)CH=CH₂ |
| A-340 | CH(CH₂—CH₃)—CH₂—CH(CH₃)—CH₃ |
| A-341 | CH(CH₂—CH₃)—CH(CH₃)—CH₂—CH₃ |
| A-342 | C(CH₃)(CH₂—CH₃)—CH₂—CH₂—CH₃ |
| A-343 | CH(i-C₃H₇)—CH₂—CH₂—CH₃ |
| A-344 | CH=C(CH₂—CH₃)—CH(CH₃)—CH₃ |
| A-345 | CH₂—C(=CH—CH₃)—CH(CH₃)—CH₃ |
| A-346 | CH₂—CH(CH=CH₂)—CH(CH₃)—CH₃ |
| A-347 | CH₂—C(CH₂—CH₃)=C(CH₃)—CH₃ |
| A-348 | CH₂—CH(CH₂—CH₃)—C(=CH₂)—CH₃ |
| A-349 | CH₂—C(CH₃)(CH=CH₂)—CH₂—CH₃ |
| A-350 | C(=CH₂)—CH(CH₂—CH₃)—CH₂—CH₃ |
| A-351 | C(CH₃)=C(CH₂—CH₃)—CH₂—CH₃ |
| A-352 | CH(CH₃)—C(=CH—CH₃)—CH₂—CH₃ |
| A-353 | CH(CH₃)—CH(CH=CH₂)—CH₂—CH₃ |
| A-354 | CH=C(CH₂—CH₃)—CH(CH₃)—CH₃ |
| A-355 | CH₂—C(=CH—CH₃)—CH(CH₃)—CH₃ |
| A-356 | CH₂—CH(CH=CH₂)—CH(CH₃)—CH₃ |
| A-357 | CH₂—C(CH₂—CH₃)=C(CH₃)—CH₃ |
| A-358 | CH₂—CH(CH₂—CH₃)—C(=CH₂)—CH₃ |
| A-359 | C(=CH—CH₃)—CH₂—CH(CH₃)—CH₃ |
| A-360 | CH(CH=CH₂)—CH₂—CH(CH₃)—CH₃ |
| A-361 | C(CH₂—CH₃)=CH—CH(CH₃)—CH₃ |
| A-362 | CH(CH₂—CH₃)CH=C(CH₃)—CH₃ |
| A-363 | CH(CH₂—CH₃)CH₂—C(=CH₂)—CH₃ |
| A-364 | C(=CH—CH₃)CH(CH₃)—CH₂—CH₃ |
| A-365 | CH(CH=CH₂)CH(CH₃)—CH₂—CH₃ |
| A-366 | C(CH₂—CH₃)=C(CH₃)—CH₂—CH₃ |
| A-367 | CH(CH₂—CH₃)—C(=CH₂)—CH₂—CH₃ |
| A-368 | CH(CH₂—CH₃)—C(CH₃)=CH—CH₃ |
| A-369 | CH(CH₂—CH₃)—CH(CH₃)—CH=CH₂ |
| A-370 | C(CH₃)(CH=CH₂)—CH₂—CH₂—CH₃ |
| A-371 | C(CH₃)(CH₂—CH₃)—CH=CH—CH₃ |
| A-372 | C(CH₃)(CH₂—CH₃)—CH₂—CH=CH₂ |
| A-373 | C[=C(CH₃)—CH₃]—CH₂—CH₂—CH₃ |
| A-374 | CH[C(=CH₂)—CH₃]—CH₂—CH₂—CH₃ |
| A-375 | C(i-C₃H₇)=CH—CH₂—CH₃ |
| A-376 | CH(i-C₃H₇)—CH=CH—CH₃ |
| A-377 | CH(i-C₃H₇)—CH₂—CH=CH₂ |
| A-378 | C(=CH—CH₃)—C(CH₃)₃ |
| A-379 | CH(CH=CH₂)—C(CH₃)₃ |
| A-380 | C(CH₃)(CH=CH₂)CH(CH₃)—CH₃ |
| A-381 | C(CH₃)(CH₂—CH₃)C(=CH₂)—CH₃ |
| A-382 | 2-CH₃-cyclohex-1-enyl |
| A-383 | [2-(=CH₂)]-c-C₆H₉ |
| A-384 | 2-CH₃-cyclohex-2-enyl |
| A-385 | 2-CH₃-cyclohex-3-enyl |
| A-386 | 2-CH₃-cyclohex-4-enyl |
| A-387 | 2-CH₃-cyclohex-5-enyl |
| A-388 | 2-CH₃-cyclohex-6-enyl |
| A-389 | 3-CH₃-cyclohex-1-enyl |
| A-390 | 3-CH₃-cyclohex-2-enyl |
| A-391 | [3-(=CH₂)]-c-C₆H₉ |
| A-392 | 3-CH₃-cyclohex-3-enyl |
| A-393 | 3-CH₃-cyclohex-4-enyl |
| A-394 | 3-CH₃-cyclohex-5-enyl |
| A-395 | 3-CH₃-cyclohex-6-enyl |

TABLE A-continued

| No. | R¹ |
|---|---|
| A-396 | 4-CH₃-cyclohex-1-enyl |
| A-397 | 4-CH₃-cyclohex-2-enyl |
| A-398 | 4-CH₃-cyclohex-3-enyl |
| A-399 | [4-(=CH₂)]-c-C₆H₉ |

The compounds I are suitable as fungicides. They are distinguished through an outstanding effectiveness against a broad spectrum of phytopathogenic fungi, especially from the classes of the Ascomycetes, Deuteromycetes, Oomycetes and Basidiomycetes. Some are systemically effective and they can be used in plant protection as foliar and soil fungicides.

They are particularly important in the control of a multitude of fungi on various cultivated plants, such as wheat, rye, barley, oats, rice, maize, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on fruit and vegetables,
*Bipolaris* and *Drechslera* species on cereals, rice and lawns,
*Blumeria graminis* (powdery mildew) on cereals,
*Botrytis cinerea* (gray mold) on strawberries, vegetables, ornamental plants and grapevines,
*Erysiphe cichoracearum* and *Sphaerotheca fuliginea* on cucurbits,
*Fusarium* and *Verticillium* species on various plants,
*Mycosphaerella* species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
*Pseudoperonospora* species on hops and cucumbers,
*Puccinia* species on cereals,
*Pyricularia oryzae* on rice,
*Rhizoctonia* species on cotton, rice and lawns,
*Septoria tritici* and *Stagonospora nodorum* on wheat,
*Uncinula necator* on grapevines,
*Ustilago* species on cereals and sugar cane, and
*Venturia* species (scab) on apples and pears.

The compounds I are also suitable for controlling harmful fungi, such as *Paecilomyces variotii*, in the protection of materials (e.g. wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 0.001 to 0.1 g, preferably 0.01 to 0.05 g, per kilogram of seed are generally necessary.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted to the usual formulations, e.g. solutions, emulsions, suspensions, dusts, powders, pastes and granules. The application form depends on the respective intended use; it should in any case guarantee a fine and uniform distribution of the compound according to the invention.

The formulations are prepared in a known way, e.g. by extending the active compound with solvents and/or carriers, if desired using emulsifiers and dispersants, it being possible, when water is the diluent, also to use other organic solvents as auxiliary solvents. Suitable auxiliaries for this purpose are essentially: solvents, such as aromatics (e.g. xylene), chlorinated aromatics (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers, such as ground natural minerals (e.g. kaolins, clays, talc, chalk) and ground synthetic ores (e.g. highly dispersed silicic acid, silicates); emulsifiers, such as nonionic and anionic emulsifiers (e.g. polyoxyethylene fatty alcohol ethers, alkylsulfonates and arylsulfonates) and dispersants, such as lignosulfite waste liquors and methylcellulose.

Suitable surfactants are alkali metal, alkaline earth metal and ammonium salts of lignosulfonic acid, naphthalenesulfonic acid, phenolsulfonic acid and dibutylnaphthalenesulfonic acid, alkylarylsulfonates, alkyl sulfates, alkylsulfonates, fatty alcohol sulfates and fatty acids, and alkali metal and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Petroleum fractions having medium to high boiling points, such as kerosene or diesel fuel, furthermore coal tar oils, and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene or isophorone, or highly polar solvents, e.g. dimethylformamide, dimethyl sulfoxide, N-methylpyrrolidone or water, are suitable for the preparation of directly sprayable solutions, emulsions, pastes or oil dispersions.

Powders, preparations for broadcasting and dusts can be prepared by mixing or grinding together the active substances with a solid carrier.

Granules, e.g. coated granules, impregnated granules and homogeneous granules, can be prepared by binding the active compounds to solid carriers. Solid carriers are, e.g., mineral earths, such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate or ureas, and plant products, such as cereal meal, tree bark meal, wood meal and nutshell meal, cellulose powders and other solid carriers.

The formulations generally comprise between 0.01 and 95% by weight, preferably between 0.1 and 90% by weight, of the active compound. The active compounds are employed therein in a purity of 90% to 100%, preferably 95% to 100% (according to the NMR spectrum).

Examples of formulations are:

I. 5 parts by weight of a compound according to the invention are intimately mixed with 95 parts by weight of finely divided kaolin. In this way, a dust comprising 5% by weight of the active compound is obtained.

II. 30 parts by weight of a compound according to the invention are intimately mixed with a mixture of 92 parts by weight of pulverulent silica gel and 8 parts by weight of liquid paraffin, which had been sprayed onto the surface of this silica gel. In this way, an active compound preparation with good adhesive properties (active compound content 23% by weight) is obtained.

III. 10 parts by weight of a compound according to the invention are dissolved in a mixture consisting of 90 parts by weight of xylene, 6 parts by weight of the addition product of 8 to 10 mol of ethylene oxide with 1 mol of the N-monoethanolamide of oleic acid, 2 parts by weight of the calcium salt of dodecylbenzenesulfonic acid and 2 parts by weight of the addition product of 40 mol of ethylene oxide with 1 mol of castor oil (active compound content 9% by weight).

IV. 20 parts by weight of a compound according to the invention are dissolved in a mixture consisting of 60 parts by weight of cyclohexanone, 30 parts by weight of isobutanol, 5 parts by weight of the addition product of 7 mol of ethylene oxide with 1 mol of isooctylphenol and 5 parts by weight of the addition product of 40 mol of ethylene oxide with 1 mol of castor oil (active compound content 16% by weight).

V. 80 parts by weight of a compound according to the invention are thoroughly mixed with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel and are ground in a hammer mill (active compound content 80% by weight).

VI. 90 parts by weight of a compound according to the invention are mixed with 10 parts by weight of N-methyl-α-pyrrolidone and a solution is obtained which is suitable for use in the form of very small drops (active compound content 90% by weight).

VII. 20 parts by weight of a compound according to the invention are dissolved in a mixture consisting of 40 parts by weight of cyclohexanone, 30 parts by weight of isobutanol, 20 parts by weight of the addition product of 7 mol of ethylene oxide with 1 mol of isooctylphenol and 10 parts by weight of the addition product of 40 mol of ethylene oxide with 1 mol of castor oil. By running the solution into 100 000 parts by weight of water and finely dispersing it therein, an aqueous dispersion is obtained comprising 0.02% by weight of the active compound.

VIII. 20 parts by weight of a compound according to the invention are thoroughly mixed with 3 parts by weight of the sodium salt of diisobutyinaphthalene-α-sulfonic acid, 17 parts by weight of the sodium salt of a lignosulfonic acid from a sulfite waste liquor and 60 parts by weight of pulverulent silica gel and are ground in a hammer mill. A spray emulsion comprising 0.1% by weight of the active compound is obtained by fine dispersion of the mixture in 20 000 parts by weight of water.

The active compounds can be used as such, in the form of their formulations or of the application forms prepared therefrom, e.g. in the form of directly sprayable solutions, powders, suspensions or dispersions, emulsions, oil dispersions, pastes, dusts, preparations for broadcasting or granules, by spraying, atomizing, dusting, broadcasting or watering. The application forms depend entirely on the intended uses; they should always ensure the finest possible dispersion of the active compounds according to the invention.

Aqueous application forms can be prepared from emulsifiable concentrates, pastes or wettable powders (spray powders, oil dispersions) by addition of water. To prepare emulsions, pastes or oil dispersions, the substances can be homogenized in water, as such or dissolved in an oil or solvent, by means of wetting agents, tackifiers, dispersants or emulsifiers. However, it is also possible to prepare concentrates comprising active substance, wetting agent, tackifier, dispersant or emulsifier and possibly solvent or oil which are suitable for dilution with water.

The concentrations of active compound in the ready-for-use preparations can be varied within relatively wide ranges. In general, they are between 0.0001 and 10%, preferably between 0.01 and 1%.

The active compounds can also be used with great success in the ultra-low volume (ULV) process, it being possible to apply formulations with more than 95% by weight of active compound or even the active compound without additives.

Oils of various types, herbicides, fungicides, other pesticides and bactericides can be added to the active compounds, if need be also not until immediately before use (tank mix). These agents can be added to the preparations according to the invention in a weight ratio of 1:10 to 10:1.

The preparations according to the invention can, in the application form as fungicides, also be present together with other active compounds, e.g. with herbicides, insecticides, growth regulators, fungicides or also with fertilizers. On mixing the compounds I or the preparations comprising them in the application form as fungicides with other fungicides, in many cases an expansion of the fungicidal spectrum of activity is obtained.

The following lists of fungicides, with which the compounds-according to the invention can be used in conjunction, is intended to illustrate the possible combinations but does not limit them:

acylalanines, such as benalaxyl, metalaxyl, ofurace or oxadixyl, amine derivatives, such as aldimorph, dodine, dodemorph, fenpropimorph, fenpropidin, guazatine, iminoctadine, spiroxamine or tridemorph, anilinopyrimidine, such as pyrimethanil, mepanipyrim or cyprodinyl, antibiotics, such as cycloheximide, griseofulvin, kasugamycin, natamycin, polyoxin or streptomycin, azoles, such as bitertanol, bromoconazole, cyproconazole, difenoconazole, dinitroconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, flutriafol, triflumizole or triticonazole, dicarboximides, such as iprodione, myclozolin, procymidone or vinclozolin, dithiocarbamates, such as ferbam, nabam, maneb, mancozeb, metam, metiram, propineb, polycarbamate, thiram, ziram or zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine, copper fungicides, such as Bordeaux mixture, copper acetate, copper oxychloride or basic copper sulfate, nitrophenyl derivatives, such as binapacryl, dinocap, dinobuton or nitrophthal-isopropyl, phenylpyrroles, such as fenpiclonil or fludioxonil, sulfur, other fungicides, such as acibenzolar-S-methyl, benthiavalicarb, carpropamid, chlorothalonil, cyflufenamid, cymoxanil, dazomet, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide, strobilurins, such as azoxystrobin, dimoxystrobin, fluoxastrobin, kresoxim-methyl, metominostrobin, orysastrobin, picoxystrobin, pyraclostrobin or trifloxystrobin, sulfenic acid derivatives, such as captafol, captan, dichlofluanid, folpet or tolylfluanid, cinnamides and analogous compounds, such as dimethomorph, flumetover or flumorph.

SYNTHESIS EXAMPLES

The procedures described in the following synthesis examples were used to prepare further compounds I by appropriate modification of the starting compounds. The compounds thus obtained are listed in the following tables, together with physical data.

1.) Synthesis of 2-cyano4-methyl-5-(2,4,6-trifluorophenyl)-6-(2-methylbutyl)pyrimidine 1.1.) 2-Methylthio-4-methyl-5-(2,4,6-trifluorophenyl)-6-chloropyrimidine

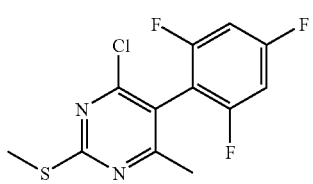

50 ml of methylmagnesium bromide solution (3 M in tetrahydrofuran) was added dropwise to a mixture of 32.5 g (0.1 mol) of 1-methylthio-4,6-dichloro-5-(2,4,6-trifluorophenyl) pyrimidine (WO 02/74753) and 0.5 g of bisdiphenylphosphinoferrocenepalladium dichloride in 150 ml of tetrahydrofuran p.a., and during the addition the reaction temperature increased to about 40° C. The reaction mixture was stirred at room temperature overnight, and saturated ammonium chloride solution was then added. The aqueous phase was extracted with methyl t-butyl ether and the combined organic phases were concentrated. The residue was purified first by chromatography using cyclohexane/methyl t-butyl ether 9:1 on silica gel and then by preparative MPLC on RP-18 silica gel. This gave 18.8 g (62%) of the title compound as a white solid.

$^1$H-NMR (CDCl$_3$, δ in ppm): 6.8 (t, 2H); 2.6 (s, 3H); 2.3 (s, 3H)

1.2.) 2-Methylthio-4-methyl-5-(2,4,6-trifluorophenyl)-6-(2-methylbutyl)pyrimidine

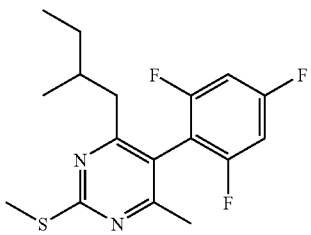

At 50° C., 70 ml (0.035 mol) of a 0.5 M solution of 2-methylbutylmagnesium bromide (in tetrahydrofuran) were added to 9.1 g (30 mmol) of 2-methylthio-4-methyl-5-(2,4,6-trifluorophenyl)-6-chloropyrimidine (Example 1.1.) and about 200 mg of bisdiphenylphosphinoferrocenepalladium dichloride in 90 ml of toluene. After about 2 hours, an additional about 200 mg of bisdiphenylphosphinoferrocenepalladium dichloride and, a little at a time, a further 50 ml of a 0.5 M solution of 2-methylbutyl-magnesium bromide (in tetrahydrofuran) were added. The reaction was monitored by HPLC.

The mixture was then hydrolyzed using saturated ammonium chloride solution, and the aqueous phase was extracted with methyl t-butyl ether. The combined organic phases were concentrated and the residue was purified by column chromatography on silica gel using cyclohexane/methyl t-butyl ether 9:1 and preparative MPLC on RP-18 silica gel. This gave 5.9 g (58%) of the title compound as a colorless oil.

$^1$H-NMR (CDCl$_3$, δ in ppm): 6.8 (t, 2H); 2.6 (s, 3H); 2.45 (dd, 1H); 2.2 (s, 3H); 2.15 (dd, 1H); 1.9 (m, 1H); 1.25 (m, 1H); 1.05 (m, 1H); 0.8 (m, 6H)

1.3.) 2-Methylsulfonyl-4-methyl-5-(2,4,6-trifluorophenyl)-6-(2-methylbutyl)pyrimidine

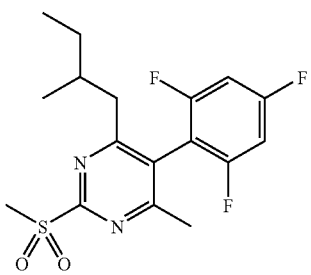

At 0° C., 2.8 g (12.3 mmol) of m-chloroperbenzoic acid (purity 77%) were added a little at a time to a solution of 1.9 g (5.6 mmol) of 2-methylthio-4-methyl-5-(2,4,6-trifluorophenyl)-6-(2-methylbutyl)pyrimidine (Example 1.2.) in 20 ml of methylene chloride p.a., and the mixture was stirred at room temperature overnight. The reaction mixture was then applied directly to a silica gel column and eluted with cyclohexane/methyl t-butyl ether 7:3. This gave 1.4 g (67%) of the title compound as a light-yellow oil.

$^1$H-NMR (CDCl$_3$, δ in ppm): 6.9 (t, 2H); 3.4 (s, 3H); 2.65 (dd, 1H); 2.45 (s, 3H); 2.4 (dd, 1H); 1.9 (m, 1H); 1.3 (m, 1H); 1.1 (m, 1H)

1.4.) 2-Cyano-4-methyl-5-(2,4,6-trifluorophenyl)-6-(2-methylbutyl)pyrimidine

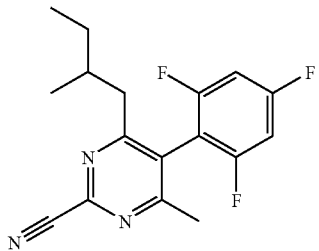

A mixture of 0.4 g (1 mmol) of 2-methylsulfonyl-4-methyl-5-(2,4,6-trifluorophenyl)-6-(2-methylbutyl)pyrimidine (Example 1.3.) and 0.2 g (3 mmol) of potassium cyanide in 20 ml of acetonitrile p.a. was stirred at 20° C. for about 16 hours. The reaction mixture was then concentrated, the residue was taken up in methylene chloride and the organic phase was extracted with water. The organic phase was concentrated and the residue was purified by column chromatography using cyclohexane/methyl t-butyl ether mixtures. This gave 0.3 g (94%) of the title compound as a colorless oil.

$^1$H-NMR (CDCl$_3$, δ in ppm): 6.9 (m, 2H); 2.6 (dd, 1H); 2.4 (s, 3H); 2.3 (dd, 1H); 1.9 (m, 1H); 1.25 (m, 1H); 1.1 (m, 1H); 0.75 (m, 6H)

TABLE I

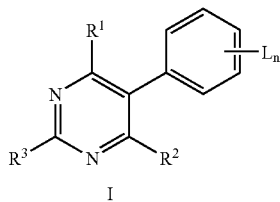

| No. | R$^1$ | R$^2$ | R$^3$ | L$_n$ | Physical data m.p. (° C.), IR (cm$^{-1}$) or NMR (ppm) |
|---|---|---|---|---|---|
| I-1 | 2-methylbutyl | chloro | cyano | 2,4,6-F$_3$ | 6.9(t, 2H); 2.7(dd, 1H), 2.4(dd, 1H); 1.9(m, 1H); 1.25 (m, 1H); 1.15(m, 1H); 0.8(m, 6H) |
| I-2 | 2-methylbutyl | cyano | cyano | 2,4,6-F$_3$ | 6.95(t, 2H); 2.8 (dd, 1H); 2.5(dd, 1H); 1.95(m, 1H); 1.25(m, 1H); 1.15 (m, 1H); 0.8(m, 6H) |
| I-3 | cyclohexyl | cyano | cyano | 2,4,6-F$_3$ | 153° C. |
| I-4 | 2-methylbutyl | methyl | cyano | 2,4,6-F$_3$ | 6.9(m, 2H); 2.6 (dd, 1H); 2.4 (s, 3H); 2.3(dd, 1H); 1.9(m, 1H); 1.25(m, 1H); 1.1 (m, 1H); 0.75 (m, 6H) |
| I-5 | but-3-enyl | methyl | cyano | 2,4,6-F$_3$ | 6.9(t, 2H); 5.9(m, 1H); 5.1(d, 1H); 5.0(d, 1H); 3.15 (t, 2H); 2.65(m, 2H); 2.5(s, 3H) |
| I-6 | 2-methylbutyl | methyl | C(=S)NH$_2$ | 2,4,6-F$_3$ | 37-41 |
| I-7 | 2-methylbutyl | methyl | C(=S)NH$_2$ | 2,4,6-F$_3$ | 45-51 |

Examples of the Action Against Harmful Fungi

The fungicidal action of the compounds of the formula I was demonstrated by the following experiments:

The active compounds were prepared as a stock solution with 0.25% by weight of active compound in acetone or DMSO. 1% by weight of the emulsifier Uniperol® EL (wetting agent having emulsifying and dispersing action based on ethoxylated alkylphenols) was added to this solution, and the solution was diluted with water to the desired concentration.

Use Examples

1. Activity against early blight of tomato caused by *Alternaria solani*, protective application Leaves of potted plants of the cultivar "Groβe Fleischtomate St. Pierre" were sprayed to runoff point with an aqueous suspension of the active compound concentration given below. The next day, the leaves were infected with an aqueous spore suspension of *Alternaria solani* in 2% biomalt solution with a concentration of 0.17×10$^6$ spores/ml. The plants were then placed in a water-vapor-saturated chamber at temperatures between 20 and 22° C. After 5 days, the early blight on the untreated but infected control plants had developed to such an extent that the infection could be determined visually in %.

The plants which had been treated with 250 ppm of the active compounds I-1, I-2, I-6 and I-7 showed less than 5% infection. The untreated control plants showed an infection of 80%.

2. Activity against gray mold on capsicum leaves caused by *Botrytis cinerea*, protective application Capsicum seedlings of the cultivar "Neusiedler Ideal Elite" were, after 4-5 leaves had fully developed, sprayed to runoff point with an aqueous suspension of the active compound concentration given below. The next day, the treated plants were inoculated with a spore suspension of *Botrytis cinerea* comprising 1.7×10$^6$ spores/ml in a 2% aqueous biomalt solution. The test plants were subsequently placed in a climatized chamber at 22 to 24° C. and high atmospheric humidity. After 5 days, the extent of the fungal infection on the leaves could be determined visually in %.

The plants which had been treated with 250 ppm of the active compounds I-1 and I-4 showed no infection. The untreated control plants showed an infection of 90%.

3. Activity against mildew on cucumber leaves caused by *Sphaerotheca fuliginea*, protective application Leaves of potted cucumber seedlings of the cultivar "Chinese snake" were, at the cotyledon stage, sprayed to runoff point with an aqueous suspension of the active compound concentration given below. 20 hours after the spray coating had dried on, the plants were inoculated with an aqueous spore suspension of mildew of cucumber (*Sphaerotheca fuliginea*). The plants were then cultivated in a greenhouse at temperatures between 20 and 24° C. and 60 to 80% relative atmospheric humidity for 7 days. The extend of the mildew development was then determined visually in % infection of the coltyledon area.

The plants which had been treated with 250 ppm of the active compounds I-2 and I-4 showed no infection. The untreated control plants showed an infection of 90%.

We claim:

1. A 2-substituted pyrimidine of the formula I

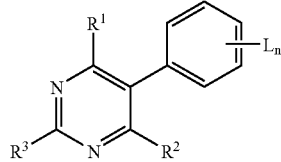

I in which the index and the substituents are as defined below:

n is an integer from 1 to 5, where at least one substituent L is located in the ortho-position on the phenyl ring;

L is halogen, cyano, cyanato (OCN), $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, —C(=O)-A, —C(=O)—O-A, —C(=O)—N(A')A, C(A')(=N—OA), N(A')A, N(A')—C(=O)-A, N(A'')-C(=O)—N(A')A, S(=O)$_m$-A, S(=O)$_m$—O-A or S(=O)$_m$—N(A')A, m is 0, 1 or 2;

A, A', A'' independently of one another are hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by cyano or $C_1$-$C_4$-alkoxy; or A and A' together with the atoms to which they are attached are a five- or six-membered saturated, partially unsaturated or aromatic heterocycle which contains one to four heteroatoms from the group consisting of O, N and S;

$R^1$ is $C_3$-$C_{10}$-alkyl, $C_3$-$C_{10}$-alkenyl, $C_3$-$C_{10}$-alkynyl, $C_3$-$C_{12}$-cycloalkyl, $C_3$-$C_{10}$-cycloalkenyl or a five- to ten-membered saturated, partially unsaturated or aromatic heterocycle which is attached via carbon and contains one to four heteroatoms from the group consisting of O, N and S, $R^2$ is halogen, cyano, $C_1$-$C_4$-alkyl, $C_2$-$C_4$-alkenyl, $C_2$-$C_4$-alkynyl, $C_1$-$C_4$-alkoxy, $C_3$-$C_4$-alkenyloxy or $C_3$-$C_4$-alkynyloxy, where the alkyl, alkenyl and alkynyl radicals of $R^2$ may be substituted by halogen, cyano, nitro, $C_1$-$C_2$-alkoxy or $C_1$-$C_4$-alkoxycarbonyl, where the aliphatic, alicyclic or aromatic groups of the radical definitions of L, $R^1$ and/or $R^2$ for their part may be partially or fully halogenated or may carry one to four groups $R^u$:

$R^u$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, —C(=O)-A, —C(=O)—O-A, —C(=O)—N(A')A, C(A')(=N—OA), N(A'), N(A')—C(=O)-A, N(A'')-C(=O)—N(A')A, S(=O)$_m$-A, S(=O)$_m$—O-A or S(=O)$_m$—N(A')A, where m, A, A', A'' are as defined above and where the aliphatic, alicyclic or aromatic groups for their part may be partially or fully halogenated or may carry one to three groups $R^v$, $R^v$ having the same meaning as $R^u$;

$R^3$ is cyano, $CO_2R^a$, $C(=O)NR^zR^b$, $C(=O)$—N—$OR^b$, $C(=NOR^a)NR^zR^b$, $C(=NR^a)NR^zR^b$, $C(=O)NR^a$—$NR^zR^b$, $C(=N$—$NR^zR^c)NR^aR^b$, $C(=O)R^a$, $C(=NOR^b)R^a$, $C(=N$—$NR^zR^b)R^a$, $CR^aR^b$—$OR^z$, $CR^aR^b$—$NR^zR^c$, ON(=$CR^aR^b$), O—C(=O)$R^a$, $NR^aR^{b'}$, $NR^a(C(=O)R^b)$, $NR^a(C(=O)OR^b)$, $NR^a(C(=O)$—$NR^zR^b)$, $NR^a(C(=NR^c)R^b)$, $NR^a(N=CR^cR^b)$, $NR^a$—$NR^zR^b$, $NR^z$—$OR^a$, $NR^a(C(=NR^c)$—$NR^zR^b)$, $NR^a(C(=NOR^c)R^b)$; where $R^a$, $R^b$, $R^c$ independently of one another are hydrogen, $C_1$-$C_6$-alkyl, $C_2$-$C_6$-alkenyl, $C_2$-$C_6$-alkynyl, $C_3$-$C_6$-cycloalkyl or $C_4$-$C_6$-cycloalkenyl;

$R^{b'}$ has the same meanings as $R^b$, except for hydrogen;

$R^z$ has the same meanings as $R^a$ and may additionally be —CO—$R^a$;

where the aliphatic or alicyclic groups of the radical definitions of $R^a$, $R^b$, $R^c$ or $R^z$ for their part may be partially or fully halogenated or may carry one to four groups $R^w$:

$R^w$ is halogen, cyano, $C_1$-$C_8$-alkyl, $C_2$-$C_{10}$-alkenyl, $C_2$-$C_{10}$-alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, and where two of the radicals $R^a$, $R^b$, $R^c$ or $R^z$ together with the atoms to which they are attached may form a five- or six-membered saturated, partially unsaturated or aromatic heterocycle which contains one to four heteroatoms from the group consisting of O, N and S.

2. A 2-substituted pyrimidine according to claim 1 where $R^2$ is chlorine, cyano, methyl, ethyl or methoxy.

3. A 2-substituted pyrimidine according to claim 1 where $R^3$ is cyano, $C(=O)NR^zR^b$, $C(=NOR^a)NR^zR^b$, $C(=NOR^b)R^a$, $C(=N$—$NR^zR^b)R^a$ or $CR^aR^b$—$NR^zR^c$.

4. A 2-substituted pyrimidine according to claim 1 where $R^3$ is ON(=$CR^aR^b$), $NR^a(C(=O)R^b)$, $NR^a(C(=O)OR^b)$, $NR^a(N=CR^cR^b)$ or $NR^z$—$OR^a$.

5. A 2-substituted pyrimidine according to claim 1 in which the phenyl group substituted by $L_n$ is the group B

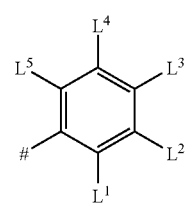

B where # is the point of attachment to the pyrimidine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, cyano, $CH_3$, $SCH_3$, $OCH_3$, $SO_2CH_3$, NH—C(=O)$CH_3$, N($CH_3$)—C(=O)$CH_3$ or $COOCH_3$ and $L^5$ is hydrogen, fluorine, chlorine or $CH_3$.

6. A process for preparing 2-substituted pyrimidines of the formula I according

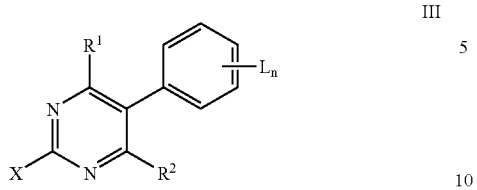

to claim 1 where $R^3$ is cyano, which comprises reacting a compound of the formula III, in which the substituents L, $R^1$ and $R^2$ are as defined in claim 1 and X is halogen, $C_1$-$C_6$-alkoxy, $C_1$-$C_6$-alkylthio, $C_1$-$C_6$-alkylsulfoxyl, $C_1$-$C_6$-alkylsulfonyl or $C_1$-$C_6$-alkylsulfenyl with a hydrocyannic acid derivative, if appropriate in the presence of a base.

7. A composition suitable for controlling harmful fungi which comprises a solid or liquid carrier and a compound of the formula I according to claim 1.

8. A method for controlling phytopathogenic harmful fungi which comprises treating the fungi or the materials, plants, the soil or seeds to be protected against fungal attack with an effective amount of a compound of the formula I according to claim 1.

9. A 2-substituted pyrimidine according to claim 2 in which the phenyl group substituted by $L_n$ is the group B

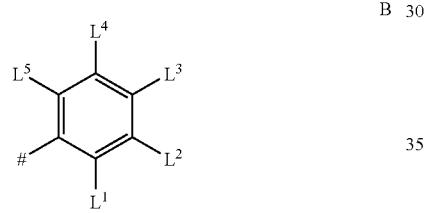

where # is the point of attachment to the pyrimidine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, cyano, $CH_3$, $SCH_3$, $OCH_3$, $SO_2CH_3$, $NH$—$C(=O)CH_3$, $N(CH_3)$—$C(=O)CH_3$ or $COOCH_3$ and $L^5$ is hydrogen, fluorine, chlorine or $CH_3$.

10. A 2-substituted pyrimidine according to claim 3 in which the phenyl group substituted by $L_n$ is the group B

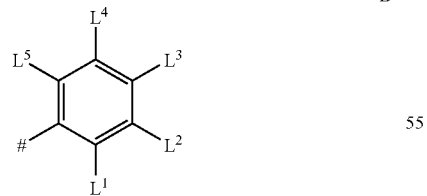

where # is the point of attachment to the pyrimidine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, cyano, $CH_3$, $SCH_3$, $OCH_3$, $SO_2CH_3$, $NH$—$C(=O)C_3$, $N(CH_3)$—$C(=O)CH_3$ or $COOCH_3$ and $L^5$ is hydrogen, fluorine, chlorine or $CH_3$.

11. A 2-substituted pyrimidine according to claim 4 in which the phenyl group substituted by $L_n$ is the group B

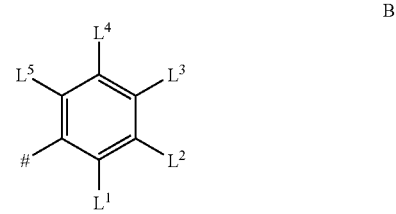

where # is the point of attachment to the pyrimidine skeleton and $L^1$ is fluorine, chlorine, $CH_3$ or $CF_3$;

$L^2$, $L^4$ independently of one another are hydrogen, $CH_3$ or fluorine;

$L^3$ is hydrogen, fluorine, chlorine, cyano, $CH_3$, $SCH_3$, $OCH_3$, $SO_2CH_3$, $NH$—$C(=O)CH_3$, $N(CH_3)$—$C(=O)CH_3$ or $COOCH_3$ and $L^5$ is hydrogen, fluorine, chlorine or $CH_3$.

12. A 2-substituted pyrimidine of the formula I

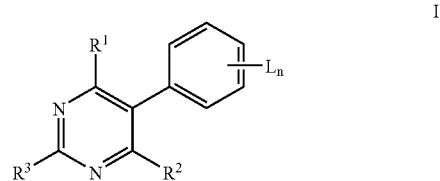

in which the index and the substituents are as defined below:

n is an integer from 1 to 5, where at least one substituent L is located in the ortho-position on the phenyl ring;

L is nitro, —C(=S)—N(A')A, or —C(NA')—SA, m is 0, 1 or 2;

A, A', A" independently of one another we hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, phenyl, where the organic radicals may be partially or fully halogenated or may be substituted by cyano or $C_1$-$C_4$-alkoxy; or A and A' together with the atoms to which they are attached are a five- or six-membered saturated, partially unsaturated or aromatic heterocycle which contains one to four heteroatoms from the group consisting of O, N and S;

$R^1$ is $C_3$-$C_{10}$-alkyl, $C_3$-$C_{10}$-alkenyl, $C_3$-$C_{10}$-alkynyl, $C_3$-$C_{12}$-cycloalkyl, $C_3$-$C_{10}$-cycloalkenyl or a five- to ten-membered saturated, partially unsaturated or aromatic heterocycle which is attached via carbon and contains one to four heteroatoms from the group consisting of O, N and S, $R^2$ is halogen, cyano, $C_1$-$C_4$-alkyl, $C_2$-$C_4$-alkenyl, $C_2$-$C_4$-alkynyl, $C_1$-$C_4$-alkoxy, $C_3$-$C_4$-alkenyloxy or $C_3$-$C_4$-alkynyloxy, where the alkyl, alkenyl and alkynyl radicals of $R^2$ may be substituted by halogen, cyano, nitro, $C_1$-$C_2$-alkoxy or $C_1$-$C_4$-alkoxycarbonyl, where the aliphatic, alicyclic or aromatic groups of the radical definitions of L, $R^1$ and/or $R^2$ for their part may be partially or fully halogenated or may carry one to four groups $R^u$:

$R^u$ is halogen, cyano, $C_1$-$C_8$-alkyl, $C_2$-$C_{10}$-alkenyl, $C_2$-$C_{10}$alkynyl, $C_1$-$C_6$-alkoxy, $C_2$-$C_{10}$-alkenyloxy, $C_2$-$C_{10}$-alkynyloxy, $C_3$-$C_6$-cycloalkyl, $C_3$-$C_6$-cycloalkenyl, $C_3$-$C_6$-cycloalkoxy, $C_3$-$C_6$-cycloalkenyloxy, —C(=O)-A, —C(=O)—O-A, —C(=O)—N(A')A, C(A')(=N—OA), N(A')A, N(A')—C(=O)-A, N(A")—C(=O)—N(A')A, S(=O)$_m$-A, S(=O)$_m$—O-A or S(=O)$_m$—N(A')A, where m, A, A', A" are as defined above and where the aliphatic, alicyclic or aromatic groups for their part may be partially or fully halogenated or may carry one to three groups R$^v$, R$^v$ having the same meaning as R$^u$;

R$^3$ is cyano, CO$_2$R$^a$, C(=O)NR$^z$R$^b$, C(=O)—N—OR$^b$, C(=S)—NR$^a$R$^b$, C(=NOR$^a$)NR$^z$R$^b$, C(=NR$^a$)NR$^z$R$^b$, C(=O)NR$^a$—NR$^z$R$^b$, C(=N—NR$^z$R$^c$)NR$^a$R$^b$, C(=O)R$^a$, C(=NOR$^b$)R$^a$, C(=N—NR$^z$R$^b$)R$^a$, CR$^a$R$^b$—OR$^z$, CR$^a$R$^b$—NR$^z$R$^c$, ON(=CR$^a$R$^b$), O—C(=O)R$^a$, NR$^a$R$^b$, NR$^a$(C(=O)R$^b$), NR$^a$(C(=O)OR$^b$), NR$^a$(C(=O)—NR$^z$R$^b$), NR$^a$(C(=NR$^c$)R$^b$), NR$^a$(N=CR$^z$R$^b$), NR$^a$—NR$^z$R$^b$, NR$^z$—OR$^a$, NR$^a$(C(=NR$^c$)—NR$^z$R$^b$), NR$^a$(C(=NOR$^c$)R$^b$); where R$^a$, R$^b$, R$^c$ independently of one another are hydrogen, C$_1$-C$_6$-alkyl, C$_2$-C$_6$-alkenyl, C$_2$-C$_6$-alkynyl, C$_3$-C$_6$-cycloalkyl or C$_4$-C$_6$-cycloalkenyl;

R$^{b'}$ has the same meanings as R$^b$, except for hydrogen;

R$^z$ has the same meanings as R$^a$ and may additionally be —CO—R$^a$;

where the aliphatic or alicyclic groups of the radical definitions of R$^a$, R$^b$, R$^c$ or R$^z$ for their part may be partially or fully halogenated or may carry one to four groups R$^w$:

R$^w$ is halogen, cyano, C$_1$-C$_8$-alkyl, C$_2$-C$_{10}$-alkenyl, C$_2$-C$_{10}$alkynyl, C$_1$-C$_6$-alkoxy, C$_2$-C$_{10}$-alkenyloxy, C$_2$-C$_{10}$-alkynyloxy, C$_3$-C$_6$-cycloalkyl, C$_3$-C$_6$-cycloalkenyl, C$_3$-C$_6$-cycloalkoxy, C$_3$-C$_6$-cycloalkenyloxy, and where two of the radicals R$^a$, R$^b$, R$^c$ or R$^z$ together with the atoms to which they are attached may form a five- or six-membered saturated, partially unsaturated or aromatic heterocycle which contains one to four heteroatoms from the group consisting of O, N and S.

13. A composition suitable for controlling harmful fungi which comprises a solid or liquid cater and a compound of the formula I according to claim 12.

14. A method for controlling phytopathogenic harmful fungi which comprises treating the fungi or the materials, plants, the soil or seeds to be protected against fungal attack with an effective amount of a compound of the formula I according to claim 12.

15. A 2-substituted pyrimidine of the formula I

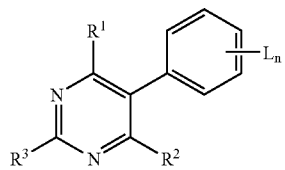

I in which the index and the substituents are as defined below:

n is an integer from 1 to 5, where at least one substituent L is located in the ortho-position on the phenyl ring;

L is halogen, cyano, cyanato (OCN), C$_1$-C$_8$-alkyl, C$_2$-C$_{10}$-alkenyl, C$_2$-C$_{10}$-alkynyl, C$_1$-C$_6$-alkoxy, C$_2$-C$_{10}$-alkenyloxy, C$_2$-C$_{10}$-alkynyloxy, C$_3$-C$_6$-cycloalkyl, C$_3$-C$_6$-cycloalkenyl, C$_3$-C$_6$-cycloalkoxy, C$_3$-C$_6$-cycloalkenyloxy, —C(=O)-A, —C(=O)—O-A, —C(=O)—N(A')A, C(A')(=N—OA), N(A')A, N(A')-C(=O)-A, N(A")-C(=O)—N(A')A, S(=O)$_m$-A, S(=O)$_m$—O-A or S(=O)$_m$—N(A')A, m is 0, 1 or 2;

A, A', A" independently of one another are hydrogen, C$_1$-C$_6$-alkyl, C$_2$-C$_6$-alkenyl, C$_2$-C$_6$-alkynyl, C$_3$-C$_8$-cycloalkyl, C$_3$-C$_8$-cycloalkenyl, phenyl, where the organic radicals may be partially or fully halogenated or may be substituted by cyano or C$_1$-C$_4$-alkoxy; or A and A' together with the atoms to which they are attached are a five- or six-membered saturated, partially unsaturated or aromatic heterocycle which contains one to four heteroatoms from the group consisting of O, N and S;

R$^1$ is C$_3$-C$_{10}$-alkyl, C$_3$-C$_{10}$-alkenyl, C$_3$-C$_{10}$-alkynyl, C$_3$-C$_{12}$-cycloalkyl, C$_3$-C$_{10}$-cycloalkenyl or a five- to ten-membered saturated, partially unsaturated or aromatic heterocycle which is attached via carbon and contains one to four heteroatoms from the group consisting of O, N and S, R$^2$ is halogen, cyano, C$_1$-C$_4$-alkyl, C$_2$-C$_4$-alkenyl, C$_2$-C$_4$-alkynyl, C$_1$-C$_4$-alkoxy, C$_3$-C$_4$-alkenyloxy or C$_3$-C$_4$-alkynyloxy, where the alkyl, alkenyl and alkynyl radicals of R$^2$ may be substituted by halogen, cyano, nitro, C$_1$-C$_2$-alkoxy or C$_1$-C$_4$-alkoxycarbonyl, where the aliphatic, alicyclic or aromatic groups of the radical definitions of L, R$^1$ and/or R$^2$ for their part may be partially or fully halogenated or may carry one to four groups R$^u$:

R$^u$ is halogen, cyano, C$_1$-C$_8$-alkyl, C$_2$-C$_{10}$-alkenyl, C$_2$-C$_{10}$-alkynyl, C$_1$-C$_6$-alkoxy, C$_2$-C$_{10}$-alkenyloxy, C$_2$-C$_{10}$-alkynyloxy, C$_3$-C$_6$-cycloalkyl, C$_3$-C$_6$-cycloalkenyl, C$_3$-C$_6$-cycloalkoxy, C$_3$-C$_6$-cycloalkenyloxy, —C(=O)-A, —C(=O)—O-A, —C(=O)—N(A')A, C(A')(=N—OA), N(A')A, N(A') -C(=O)-A, N(A")-C(=O)—N(A')A, S(=O)$_m$-A, S(=O)$_m$—O-A or S(=O)$_m$—N(A')A, where m, A, A', A" are as defined above and where the aliphatic, alicyclic or aromatic groups for their part may be partially or fully halogenated or may carry one to three groups R$^v$, R$^v$ having the same meaning as R$^u$;

R$^3$ is C(=S)—NR$^a$R$^b$; where

R$^a$ and R$^b$, independently of one another are hydrogen, C$_1$-C$_6$-alkyl, C$_2$-C$_6$-alkenyl, C$_2$-C$_6$-alkynyl, C$_3$-C$_6$-cycloalkyl or C$_4$-C$_6$-cycloalkenyl;

where the aliphatic or alicyclic groups of the radical definitions of R$^a$ and R$^b$ for their part may be partially or fully halogenated or may carry one to four groups R$^w$;

R$^w$ is halogen, cyano, C$_1$-C$_8$-alkyl, C$_2$-C$_{10}$-alkenyl, C$_2$-C$_{10}$-alkynyl, C$_1$-C$_6$-alkoxy, C$_2$-C$_{10}$-alkenyloxy, C$_2$-C$_{10}$-alkynyloxy, C$_3$-C$_6$-cycloalkyl, C$_3$-C$_6$-cycloalkenyl, C$_3$-C$_6$-cycloalkoxy, C$_3$-C$_6$cycloakenyloxy, and where two of the radicals R$^a$ and R$^b$ together with the atoms to which they are attached may form a five- or six-membered saturated, partially unsaturated or aromatic heterocycle which contains one to four heteroatoms from the group consisting of O, N and S.

16. A composition suitable for controlling harmful fungi which comprises a solid or liquid carrier and a compound of the formula I according to claim 15.

17. A method for controlling phytopathogenic harmful fungi which comprises treating the fungi or the materials, plants, the soil or seeds to be protected against fungal attack with an effective amount of a compound of the formula I according to claim 15.

* * * * *